US010692148B1

(12) United States Patent
Piacentile

(10) Patent No.: US 10,692,148 B1
(45) Date of Patent: Jun. 23, 2020

(54) SYSTEMS AND METHODS FOR WIRELESS JOURNAL PRESENTATION

(76) Inventor: Joseph Piacentile, Fort Lee, NJ (US)

( * ) Notice: Subject to any disclaimer, the term of this patent is extended or adjusted under 35 U.S.C. 154(b) by 1150 days.

(21) Appl. No.: 11/067,150

(22) Filed: Feb. 25, 2005

Related U.S. Application Data

(63) Continuation-in-part of application No. 10/951,212, filed on Sep. 27, 2004, now Pat. No. 8,694,329.

(60) Provisional application No. 60/506,698, filed on Sep. 26, 2003.

(51) Int. Cl.
| *G06Q 40/08* | (2012.01) |
| *G06Q 30/02* | (2012.01) |
| *G16H 40/20* | (2018.01) |
| *G16H 20/13* | (2018.01) |
| *G16H 10/20* | (2018.01) |
| *G16H 10/60* | (2018.01) |

(52) U.S. Cl.
CPC ............. *G06Q 40/08* (2013.01); *G06Q 30/02* (2013.01); *G16H 10/20* (2018.01); *G16H 10/60* (2018.01); *G16H 20/13* (2018.01); *G16H 40/20* (2018.01)

(58) Field of Classification Search
CPC ........ G06Q 50/24; G06Q 30/02; G06Q 40/08; G06Q 50/22; G06Q 30/0201; G06Q 30/0202; G06Q 30/0204; G06Q 30/0252; G06Q 30/04; G06Q 30/0629; G16H 10/20; G16H 10/60; G16H 50/20; G16H 40/20; G16H 20/10; G16H 20/13; G16H 50/70
See application file for complete search history.

(56) References Cited

U.S. PATENT DOCUMENTS

| 4,774,655 | A | * | 9/1988 | Kollin | ..................... G06F 16/38 |
| 5,016,172 | A | | 5/1991 | Dessertine | |
| 5,408,443 | A | | 4/1995 | Weinberger | |
| 5,722,418 | A | | 3/1998 | Bro | |
| 5,737,539 | A | | 4/1998 | Edelson et al. | |
| 5,845,255 | A | * | 12/1998 | Mayaud | .............. G06F 19/3456 |
| | | | | | 705/3 |
| 5,995,939 | A | | 11/1999 | Berman et al. | |
| 6,347,329 | B1 | * | 2/2002 | Evans | .......................... 709/202 |
| 6,421,675 | B1 | | 7/2002 | Ryan et al. | |
| 6,482,156 | B2 | | 11/2002 | Iliff | |
| 6,564,121 | B1 | | 5/2003 | Wallace et al. | |

(Continued)

OTHER PUBLICATIONS

"U.S. Appl. No. 10/951,212, Advisory Action dated Nov. 8, 2010", 2 pgs.

(Continued)

*Primary Examiner* — Neal Serebloff
(74) *Attorney, Agent, or Firm* — FisherBroyles, LLP; Ariel Reinitz

(57) ABSTRACT

A medical information system informs prescribers of medical journal publication information in a system for preparing a prescription. The point of prescribing messaging system can assist physicians in selecting medications when prescribing medication for patients by reviewing pertinent articles displayed with the apparatus. The system may include a point of prescription application configured to order, access and display medical journal articles based on associations between the articles and medical information identifiers including patient treatment, diagnosis or drug information managed by the apparatus. A data structure maintained or accessed by the system contain the associations or references for accessing the medical journal publication information.

33 Claims, 26 Drawing Sheets

(56) References Cited

U.S. PATENT DOCUMENTS

| | | | |
|---|---|---|---|
| 6,656,122 | B2 | 12/2003 | Davidson et al. |
| 6,684,188 | B1 | 1/2004 | Mitchell et al. |
| 6,694,334 | B2 | 2/2004 | DuLong et al. |
| 6,717,598 | B1 | 4/2004 | Melton, Jr. et al. |
| 6,735,497 | B2 | 5/2004 | Wallace et al. |
| 8,694,329 | B1 | 4/2014 | Piacentile |
| 2002/0032583 | A1 | 3/2002 | Joao |
| 2002/0042725 | A1 | 4/2002 | Mayaud |
| 2002/0042726 | A1* | 4/2002 | Mayaud .............. G06F 19/3456 705/2 |
| 2002/0165736 | A1 | 11/2002 | Tolle et al. |
| 2003/0036683 | A1* | 2/2003 | Kehr .................... G06F 19/325 600/300 |
| 2003/0050802 | A1 | 3/2003 | Jay et al. |
| 2003/0167190 | A1 | 9/2003 | Rincavage et al. |
| 2004/0002872 | A1* | 1/2004 | Wright ................ G06F 19/3418 705/2 |
| 2004/0172295 | A1 | 9/2004 | Dahlin et al. |
| 2004/0267566 | A1* | 12/2004 | Badgett et al. ................... 705/2 |
| 2006/0265245 | A1 | 11/2006 | Mccallie et al. |

OTHER PUBLICATIONS

"U.S. Appl. No. 10/951,212, Final Office Action dated Mar. 2, 2010", 43 pgs.
"U.S. Appl. No. 10/951,212, Final Office Action dated Oct. 6, 2011", 38 pgs.
"U.S. Appl. No. 10/951,212, Non Final Office Action dated Apr. 15, 2009", 52 pgs.
"U.S. Appl. No. 10/951,212, Non Final Office Action dated May 15, 2013", 36 pgs.
"U.S. Appl. No. 10/951,212, Non Final Office Action dated Dec. 22, 2010", 43 pgs.
"U.S. Appl. No. 10/951,212, Notice of Allowance dated Feb. 7, 2014", 17 pgs.
"U.S. Appl. No. 10/951,212, Notice of Allowance dated Feb. 27, 2014", 14 pgs.
"U.S. Appl. No. 10/951,212, Response filed Jun. 21, 2011 to Non Final Office Action dated Dec. 22, 2010", 33 pgs.
"U.S. Appl. No. 10/951,212, Response filed Oct. 11, 2010 to Final Office Action dated Mar. 2, 2010", 21 pgs.
"U.S. Appl. No. 10/951,212, Response filed Oct. 15, 2009 to Non Final Office Action dated Apr. 15, 2009", 20 pgs.
"U.S. Appl. No. 10/951,212, Response filed Oct. 15, 2013 to Non Final Office Action dated May 15, 2013", 13 pgs.
"U.S. Appl. No. 10/951,212, Response filed Nov. 2, 2012 to Final Office Action dated Oct. 6, 2011", 17 pgs.
"U.S. Appl. No. 11/065,735, Advisory Action dated Oct. 10, 2013", 3 pgs.
"U.S. Appl. No. 11/065,735, Advisory Action dated Nov. 9, 2010", 3 pgs.
"U.S. Appl. No. 11/065,735, Examiner Interview Summary dated May 16, 2013", 3 pgs.
"U.S. Appl. No. 11/065,735, Examiner Interview Summary dated Dec. 11, 2012", 3 pgs.
"U.S. Appl. No. 11/065,735, Examiner Interview Summary dated Dec. 27, 2013", 3 pgs.
"U.S. Appl. No. 11/065,735, Final Office Action dated Feb. 16, 2016", 18 pgs.
"U.S. Appl. No. 11/065,735, Final Office Action dated Mar. 15, 2013", 20 pgs.
"U.S. Appl. No. 11/065,735, Final Office Action dated Oct. 24, 2011", 20 pgs.
"U.S. Appl. No. 11/065,735, Final Office Action dated Nov. 12, 2009", 16 pgs.
"U.S. Appl. No. 11/065,735, Non Final Office Action dated Jan. 5, 2011", 17 pgs.
"U.S. Appl. No. 11/065,735, Non Final Office Action dated Jan. 9, 2009", 14 pgs.
"U.S. Appl. No. 11/065,735, Non Final Office Action dated Oct. 5, 2016", 17 pgs.
"U.S. Appl. No. 11/065,735, Non Final Office Action dated Dec. 30, 2014", 18 pgs.
"U.S. Appl. No. 11/065,735, Response filed Apr. 5, 2017 to Non Final Office Action dated Oct. 5, 2016", 25 pgs.
"U.S. Appl. No. 11/065,735, Response filed Jun. 30, 2015 to Non Final Office Action dated Dec. 30, 2014", 11 pgs.
"U.S. Appl. No. 11/065,735, Response filed Jul. 1, 2011 to Non Final Office Action dated Jan. 5, 2011", 26 pgs.
"U.S. Appl. No. 11/065,735, Response filed Jul. 9, 2009 to Non Final Office Action dated Jan. 9, 2009", 15 pgs.
"U.S. Appl. No. 11/065,735, Response filed Aug. 16, 2016 to Final Office Action dated Feb. 16, 2016", 22 pgs.
"U.S. Appl. No. 11/065,735, Response filed Sep. 15, 2013 to Final Office Action dated Mar. 15, 2013", 10 pgs.
"U.S. Appl. No. 11/065,735, Response filed Oct. 11, 2010 to Final Office Action dated Nov. 12, 2009", 13 pgs.
"U.S. Appl. No. 11/065,735, Response filed Nov. 19, 2012 to Final Office Action dated Oct. 24, 2011", 7 pgs.
"U.S. Appl. No. 14/247,174, Final Office Action dated Mar. 10, 2016", 25 pgs.
"U.S. Appl. No. 14/247,174, Non Final Office Action dated Jun. 3, 2015", 22 pgs.
"U.S. Appl. No. 14/247,174, Non Final Office Action dated Dec. 29, 2016", 24 pgs.
"U.S. Appl. No. 14/247,174, Preliminary Amendment filed Apr. 7, 2014", 7 pgs.
"U.S. Appl. No. 14/247,174, Response filed Sep. 12, 2016 to Final Office Action dated Mar. 10, 2016", 21 pgs.
"U.S. Appl. No. 14/247,174, Response filed Dec. 3, 2015 to Non Final Office Action dated Jun. 3, 2015", 9 pgs.

* cited by examiner

| Trigger Medication | Target Alternative | Message | Sponsor | Conditions |
|---|---|---|---|---|
| Medication-A | Medication-B | Message-1 | B | |
| Medication-A | Medication-BB | Message-1 | B | |
| Medication-A | Medication-BBB | Message-2 | B | |
| Medication-A | Medication-C | Message-3 | C | |
| Medication-A | Medication-CC | Message-3 | C | |
| Medication-A | Medication-AA | Message-4 | A | |
| Medication-C | Medication-A | Message-4 | A | |
| Medication-C | Medication-AA | Message-4 | A | |
| Medication-C | Medication-BB | Message-1 | B | |

FIG. 23

| | | | | Condition 1 | Condition 2 | Condition 3 | Condition 4 |
|---|---|---|---|---|---|---|---|
| Trigger Medication | Target Alternative | Message | Sponsor | Age | Gender | Region | Date |
| Medication-A | Medication-B | Message-1 | B | 18 and over | M or F | All | Any |
| Medication-A | Medication-BB | Message-1 | B | under 18 | M or F | Southern | after 1/1/2001 |
| Medication-A | Medication-BBB | Message-2 | B | 2 and over | M or F | Northern | before 1/1/2001 |
| Medication-A | Medication-C | Message-3 | C | 2 to 40 | M | Western | 2/2001 to 2/2004 |
| Medication-A | Medication-CC | Message-3 | C | 2 and over | F | W. and S. | Any |
| Medication-A | Medication-AA | Message-4 | A | 18 and over | M or F | Eastern | Any |
| Medication-C | Medication-A | Message-4 | A | 2 and over | M or F | All | Any |
| Medication-C | Medication-AA | Message-4 | A | 18 and over | M or F | Eastern | Any |
| Medication-C | Medication-BB | Message-1 | B | under 18 | M or F | Southern | after 1/1/2001 |

FIG. 24

| Trigger Medication | Target Alternative | Message | Sponsor | Journal | Condition 1 Age | Condition 1 ... | Condition 5 Publishing Date |
|---|---|---|---|---|---|---|---|
| Medication-A | Medication-B | Message-1 | B | | 18 and over | | |
| Medication-A | Medication-BB | Message-1 | B | | under 18 | | All |
| Medication-A | Medication-BBB | Message-2 | B | Article1 | 2 and over | | All |
| Medication-AA | | | | Article2 | | | recent (30 days) |
| Medication-AAA | | | | Article3 | | | |
| | | | | | | | |
| | | | | | | | |
| | | | | | | | |

FIG. 25

SYSTEMS AND METHODS FOR WIRELESS JOURNAL PRESENTATION

CROSS REFERENCE TO RELATED APPLICATIONS

This application is a continuation in part application of pending U.S. patent application Ser. No. 10/951,212, filed Sep. 27, 2004, and claims the benefit of the filing date of U.S. Provisional Patent Application No. 60/506,698 filed Sep. 26, 2003, the disclosures of which are hereby incorporated herein by reference. This application also incorporates herein by reference the disclosure of U.S. patent application Ser. No. 11/065,735, filed Feb. 25, 2005, and entitled "Systems and Methods for Wireless Prescription Compliance Monitoring."

BACKGROUND OF THE INVENTION

The method by which a patient fills a prescription written by his or her doctor has become increasingly complex in the modern health care environment. Most patients with medical insurance must deal with a health care system having four components: an insurer, a physician who is enrolled in the insurer's network, service providers such as pharmacies, hospitals, etc., and the pharmacy benefit manager (PBM)—a management company that manages the pharmacy benefits of the insurer.

The PBM compiles a formulary of medications for the insurer (i.e., a list of medications that the insurer will cover for their enrolled members or that they prefer their members to use for given diagnosis.) In addition, the PBM maintains patient medication histories and other pertinent information related to the safety of the formulary medications for each member. Each PBM is electronically connected to the majority of pharmacies in the nation.

When a prescription is presented at a pharmacy, the pharmacy computer connects to the PBM that manages the pharmacy benefits for that patient. The PBM provides data such as eligibility information, plan details, co-payment requirements and generic options to the inquiring pharmacy. Additionally, the PBM checks to see whether the prescribed medication is within the benefit plan's formulary, and executes a Drug Utilization Review (DUR), which analyzes the prescribed medication versus the patient's known medication and medical history (drug to drug, drug to allergy, drug to medical condition, etc.)

A number of problems can occur during this process if the PBM detects a conflict or potential conflict with the presented script. Formulary variance or contraindication will cause the PMB to signal a notification to the pharmacist. Usually, the pharmacist will make one or more phone calls to the physician to request a change in the prescription in order to make it compliant with the plan, or consistent with the DUR notification. The pharmacist will speak directly to the physician to request any changes being made to the prescription, and any changes are usually entered into the patient's chart. Thus, the current prescription delivery system is increasingly hampered by escalating numbers of necessary phone calls to resolve these prescription-related issues, each of which encroaches on both the pharmacist's and the physician's time.

One attempt to improve the prescription process requires installing custom prescription management software on a local computer within a physician's office, which has the capability of communicating with a remote PBM computer. A physician enters a prescription on a patient's chart, and gives the chart to a staff member (the "user") who enters the prescription information on one or more data entry screens on the local computer. The software directs the local system to connect with the PBM to determine formulary compliance and to perform a DUR. Any problems with the prescription are conveyed to the user, who must then communicate the difficulty to the physician. The physician alters the prescription, and the user repeats the process until an acceptable prescription is found.

Though this approach does reduce the previously required physician-directed phone calls, it still causes considerable disruption. Each time the system indicates a problem, which may occur several times for a single prescription, the user must leave the computer, find and interrupt the physician, and ask that changes be made. It is primarily for this reason that such a system has not been overwhelmingly adopted.

Such systems also do not provide sufficient means for informing prescribers about medications (new or otherwise) that may be appropriately used by their patients for any given problem when prescribing. Traditionally, physicians become aware of potential alternative medications in various ways. Drug sponsors often send sales representatives to meet with prescribers or otherwise send literature to inform them about new medications and treatments. However, such methods tend to inundate prescribers with too much information relating to too many different medications such that the volume of information renders the presentation of information for any individual drug ineffective. Moreover, such information may be presented at inopportune times when the prescriber is not prepared to consider the new drug information or simply is unable to schedule a meeting with a particular representative. It may be desirable to have improvements to these systems for informing prescribers of medicines and alternatives thereto in an electronic prescribing environment while avoiding problems that may result from medication conflicts indicated by a DUR and/or the requirements of a patient or plan specific formulary.

SUMMARY OF THE INVENTION

The invention relates to an automated system for assisting physicians. The system permits physicians and prescribers to be offered or to view or access to medical journal publications articles with a prescription generating application. For example, the system automatically displays relevant medical journal publication messages in response to the physician's initiation of a prescription as a way of educating physicians and prescribers about alternative medications at the time of prescribing.

Preferably, real-time wireless communication is used to communicate patient specific information, medical journal information and medication specific information to and from remote systems maintaining this information and the physician's prescribing device. Alternatively, the prescribing device can be initialized (synchronized) through wired connector of a cradle at times at beginning of and during the day with patient information, patient's medicines and alternatives for high-speed high volume data transfer and re-synchronized to server with script or prescription information throughout the day, again through a cradle, or alternatively through wireless transmission.

In such an example system an embodiment of an invention including a preferred method for prescribing a drug electronically may be implemented to inform a prescriber about a medical journal publication. The method includes receiving an indicator of a medication to be prescribed to a patient. The method also includes identifying medical journal publication data based on accessing a data structure that determines associations between medical information identifiers and medical journal publication data. The system prompts for a response to indicate whether or not the medication of the indicator should be prescribed to the patient. The method also generates a prescription for the patient in response to the prompting. Optionally, method of may include displaying medical journal publication data in response to input requesting a presentation of the medical journal publication data.

The medical information identifiers may be treatment information, diagnosis information or drug information, for example. In a version of the system, identifying may be in response to a selection of a patient for prescription. Additionally, orders may be generated for further medical journal publication data based on authentication information to purchase or otherwise gain access to text of a medical journal article that was only previously identified by title, author, summary etc.

Another embodiment, a method of presenting medical journal publication data to a user of a drug prescription system may involve maintaining data of medical information identifiers with references to medical journal publication information. The method provides a prescription application configured for accepting a drug identifier input request and for electronically generating a prescription with the drug identifier input request. The prescription application can be further configured for controlling requesting medical journal publication information from the data based on medical information identifiers managed by the prescription application. Additionally, the prescription application may be configured for controlling presenting the medical journal publication information for display.

Moreover, the method may include receiving requests with medical information identifiers and sending responses with medical journal publication information based on the references of the data. Charge information may be processed in association with a request for medical journal publication information and text of an article may be provided.

In another example, an apparatus for generating electronic prescriptions and informing prescribers of medication information may include a user interface for accepting medication selections for inclusion in an electronic prescription. The apparatus also has a messaging controller for displaying medical journal publication information. The apparatus also includes a prescription generator configured for forming an electronic prescription with the medication. In the apparatus, optionally the messaging controller may be configured for determining medical journal publication information by accessing a data structure relating medical information identifiers and medical journal publication information. The accessing may be performed by communication with a remote device on a network or the data structure may be stored on the apparatus. The messaging controller may be optionally configured for displaying medical journal publication information based on a patient's treatment, diagnosis information or a selection of a drug for potential use by the patient.

In one embodiment of a system for generating electronic prescriptions and informing prescribers of medication information in a journal publication article, the system includes means for maintaining a data structure of medical information including trigger information being referenced to a target medical journal publication information. Additionally, the preferred system has means for selecting a first drug selection for a prescription and means for determining from the data structure at least one of the referenced target medical journal publication information for presenting in response to the trigger information. The system may also include means for presenting a message suggesting medical journal publication information and means for permitting the user to generate the prescription. In several variations, the system may be configured for displaying medical journal publication information based on a drug chosen for prescription, a patient's diagnosis and/or a patient's treatment. Such a presentation of the medical journal article may be automated in response to a selection of a patient for prescription or in response to a selection of drug for prescription. Additional aspects of the invention will be apparent from a review of the drawings, the following disclosure, and the claims.

BRIEF DESCRIPTION OF THE DRAWINGS

FIG. 23 is an illustrated table data structure assessable to the point of prescription application with associated selected or trigger medications and target or alternative suggested medications of different brands or generic names of various different sponsors (e.g., A, B and C);

FIG. 24 is another example table data structure assessable by the point of prescription application with associations between trigger and target medications also illustrating additional conditions for displaying messages concerning the target medications; and FIG. 25 is another example table data structure illustrating the storage of a journal article in association with other data.

DETAILED DESCRIPTION

Figure 1:
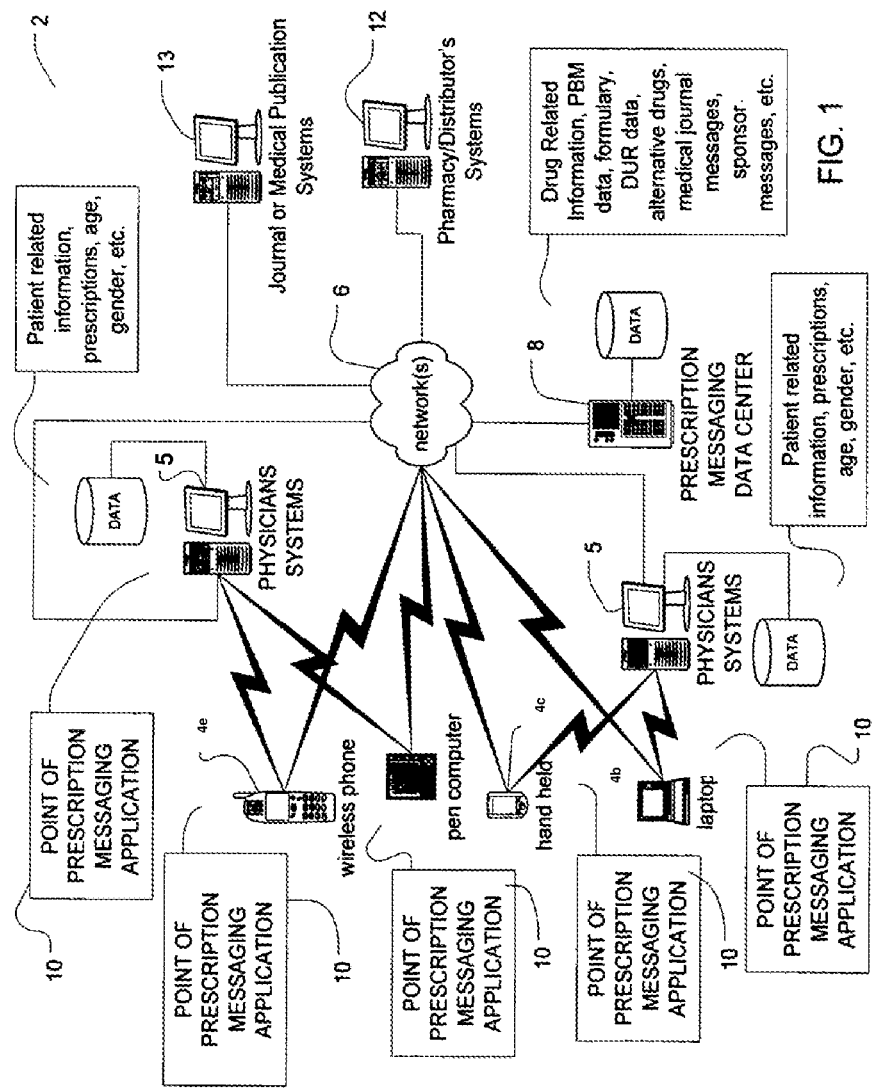
FIG. 1 is a network diagram of an example embodiment including preferred components of a physician assist system of the invention including a point of prescription application.

Referring to the figures, where like numerals indicate similar features, a physician assist system 2 for electronic prescribing of the invention typically includes a prescribing device(s) 4, preferably accessible to a physician, such as a desktop 4a, laptop 4b, hand held or palm computer 4c, a personal data assistant (PDA) 4d or other programmable input/output processing device such as a smart mobile phone 4e. The physician assessable prescribing device 4 may optionally be configured for connection or networking to other systems or computers via one or more communications mechanisms. While such communication links may in pan implemented as a physical connection such as a telephone line, cable or contact based (e.g., cradle) hook-up, in a preferred embodiment, the prescribing device 4 at least includes a communications mechanism that can link the device to other systems via a wireless communications channel. For example, the device may be configured for Bluetooth networking and/or communications over a cellular telephone network for transmitting data or voice. Where such networked communications involve transfer of signals or messages over one or more network(s) 6 that includes an open-type network, such as an internet or the Internet, preferably such signals or messages are encrypted. The network(s) 6 may also include a telephone network, for example, in the event that facsimile transmissions are utilized in the transmission of prescription related messages as discussed in more detail herein.

Figure 2:
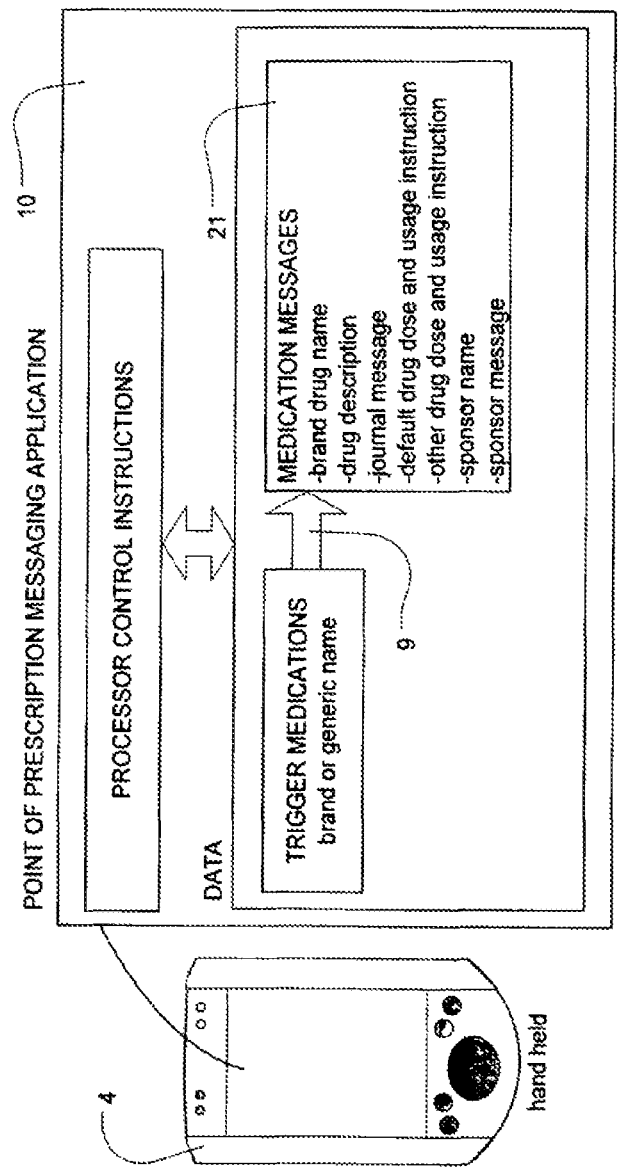
FIG. 2 is an representation of a preferred point of prescription messaging application in a prescribing device with data associations between trigger medications and journal messages.

As illustrated in FIG. 2, the physician accessible prescribing device 4 generally includes a processor and memory with processor control instructions and/or other application specific electronic control circuitry. Preferably, such components are for implementing functionality of a point of prescription messaging application 10 of the physician assist system 2. As will be explained in more detail herein, generally, such application will access or control displaying of medication related messages 21, such as informing a user of existence of one or more journal articles or studies, based on medication associations 9 which relate the messages to a medication selected for prescription.

The physician assist system 2 may also include a prescription messaging data center server 8. The data center server 8 is also preferably equipped with one or more communications devices for communication with one or more physician accessible prescribing devices 4 having point of prescription applications 10. This communication between the data center server 8 and the physician accessible prescribing device may be direct or indirect. Generally, the data center server 8 will include processor control instructions for communications between physician accessible prescribing devices 4 for prescription related data exchange as will be described in more detail below. Of course, the data center server 8 may be implemented by multiple servers accessible over open and/or private or otherwise secure networks. The database of such a prescription messaging data center server may optionally include the information of a PBM or otherwise have access to a PBM over the network 6. Furthermore, the database of the prescription messaging data center server 8 may also include alternative drug associations and messages associated with recommending such alternative drugs to physicians as will be explained in more detail herein. It may also include data associated with medical journal articles or links or references to journal articles stored elsewhere (e.g., via URLs) and associations between them and drugs, diagnoses, treatment or other medical information identifiers.

In general, the physician assist system 2 may also include distribution related systems such as one or more servers associated with pharmacy systems 12. Generally, the pharmacy system 12 is accessible by the network 6. It is preferred that the pharmacy system 12 be enabled for receiving or processing prescription requests or orders for distribution of medication to a patient of the physician. Thus, in a typical arrangement, the pharmacy system 12 may electronically receive a prescription over the network 6. Since this information is preferred to be confidential, such electronic communication may be via encrypted electronic data messaging or other secured communication such as a telephone facsimile transmission received by the pharmacy system 12.

In general, the physician assist system 2 may also include journal or medical publication related systems such as one or more servers associated with a journal publishing system 13. Generally, the journal publishing system 13 is accessible by the network 6. It is preferred that the journal publishing system 13 be enabled for receiving or processing journal or medical publication requests or orders. Thus, in a typical arrangement, the journal publishing system may electronically receive a request or order for a journal article over the network 6 and return a response containing information about or including a journal or medical article publication. Thus, the journal publishing system 13 may electronically transfer an article to a prescribing device or transmit the article by some other means, for example, by facsimile to the prescriber. Preferably, such journal or medical article publications can be obtained in a database or other data storage device and data structure. The system may also be equipped or programmed to charge account information associated with a particular prescriber for purposes of processing any monetary charge that may be associated with the request or order for the journal article by the prescriber.

Other arrangements of the components of such a physician assist system 2 will be apparent to those skilled in the art. For example, the components may be arranged as the electronic prescription system disclosed in U.S. patent application Ser. No. 09/653,123 filed Aug. 31, 2000, the contents of which have been incorporated herein by reference.

In general, such systems will share electronic patient information and drug/medication information as discussed herein, which may be stored in various devices or databases of the system. Data sharing between such systems may be periodic as in a synchronization scheme. Such sharing may also be transferred by a communication means as needed when such information is requested at any given time by a device of the system.

As previously discussed, the physician accessible prescribing device 2 of the system when equipped for entering electronic prescriptions includes a point of prescription messaging application 10. A description of an operation controlled by the control code of such an application will now be described with respect to a preferred embodiment.

Figure 3:
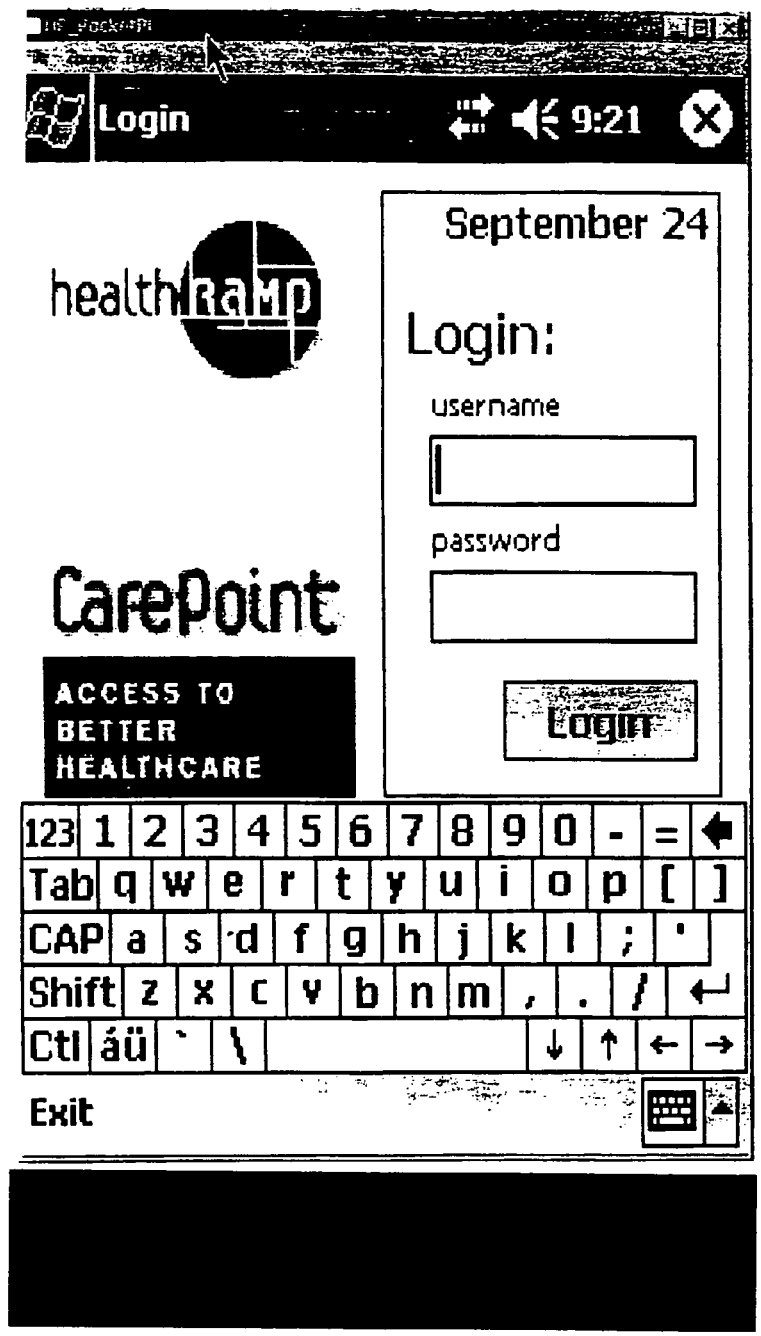
FIG. 3 is a user interface of a point of prescription application illustrating a prescriber login to a physician assist system of the invention.
Figure 4:
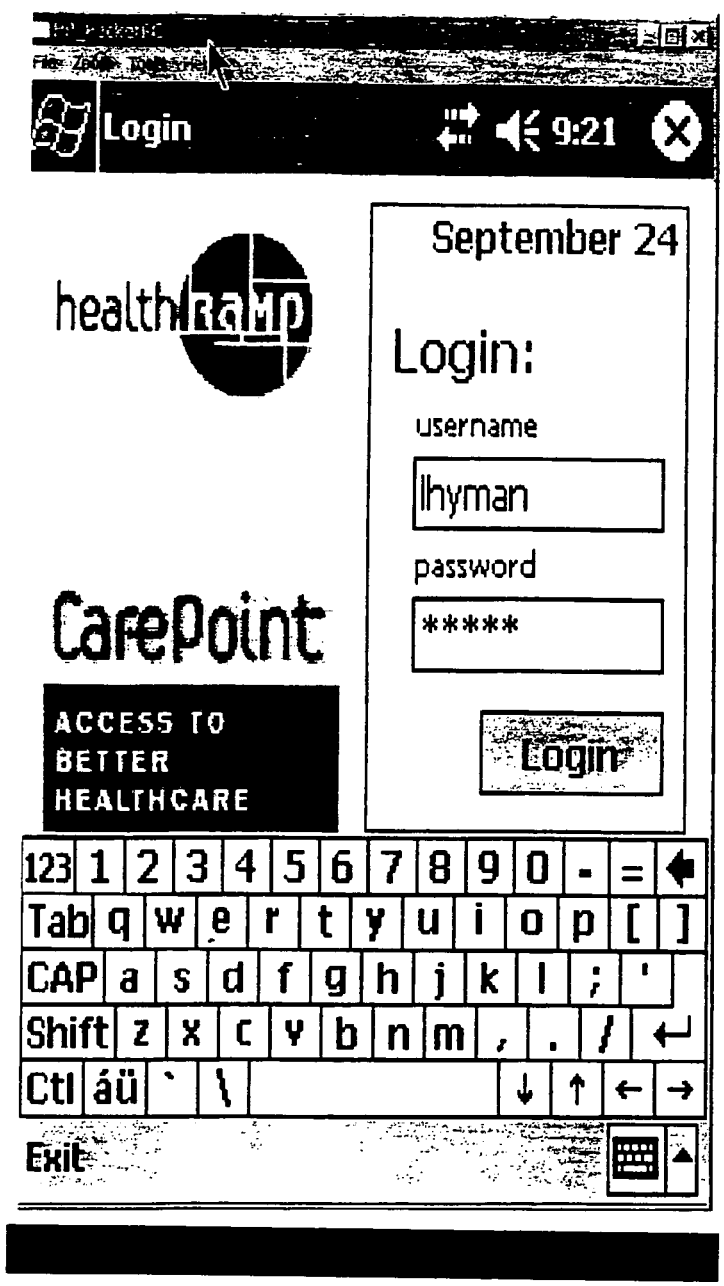
FIG. 4 is a the user interface of FIG. 3 after entry of username and password.
Figure 5:
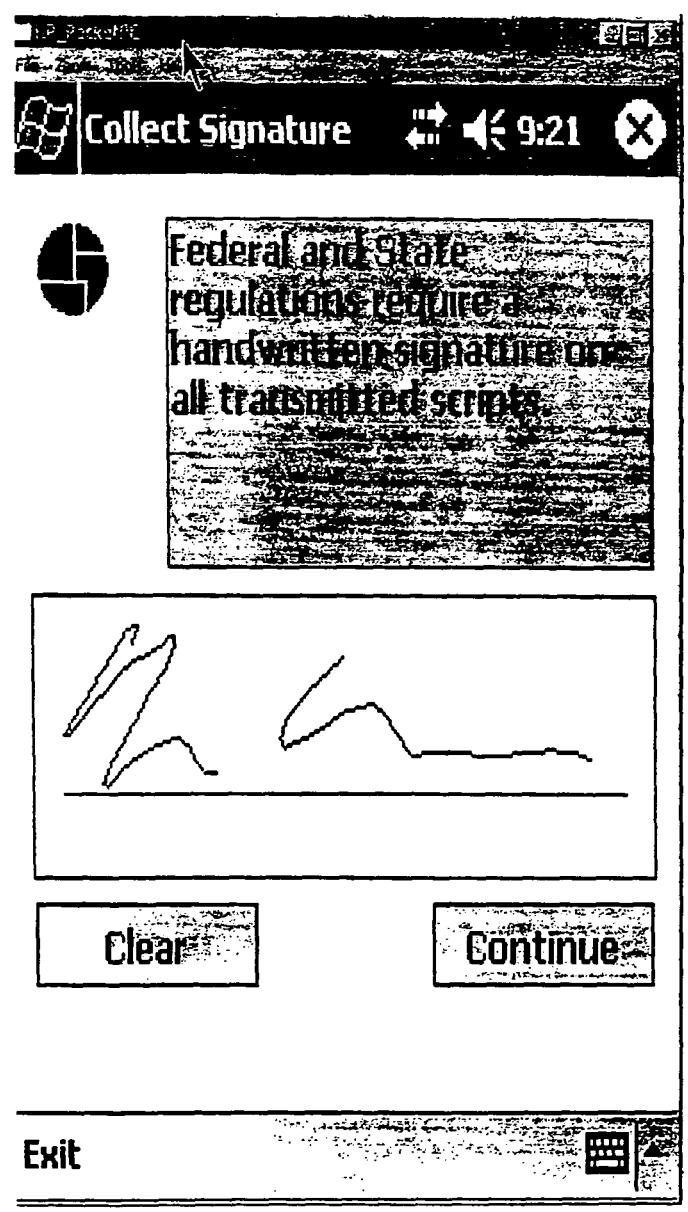
FIG. 5 is a signature input user interface of a point of prescription application corresponding to the login procedure of the physician assist system of the invention.
Figure 6:
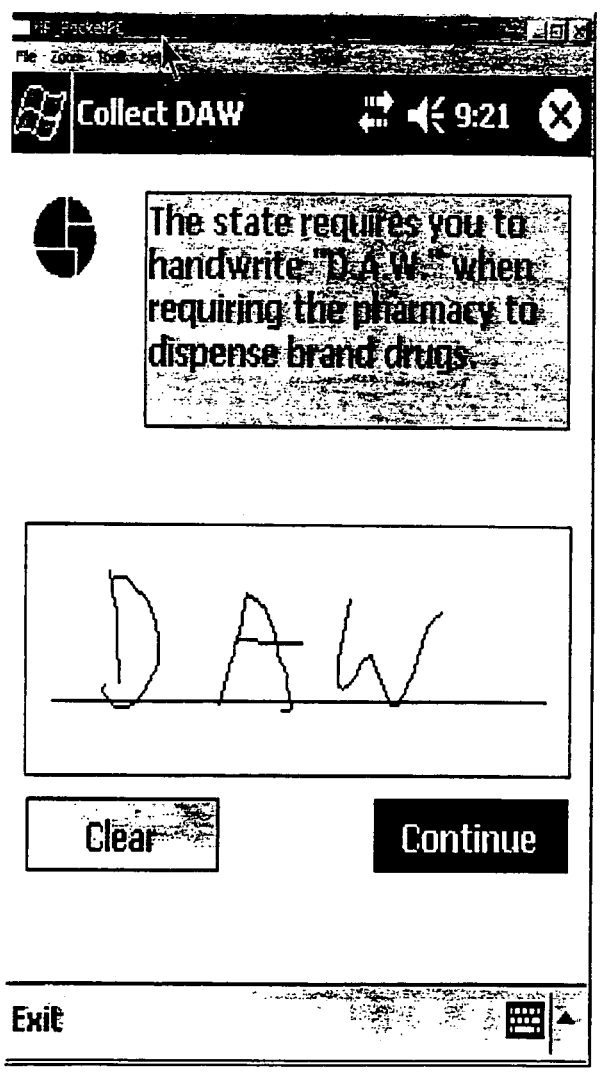
FIG. 6 is a further login screen of a point of prescription application used in authorizing electronic prescribing of drugs in the physician assist system of the invention.

In this example of operation, a physician-prescriber operates prescribing device 4 with the physician assist system for the purpose of prescription generation as illustrated with regard to the user interface illustrations of FIGS. 3 to 22. Initially, for security purposes, a login screen is displayed (FIG. 3) prompting the prescriber to enter login information. Logging in preferably includes entering login information which may include electronic signature and/or a handwriting samples (FIGS. 4-6).

Figure 7:
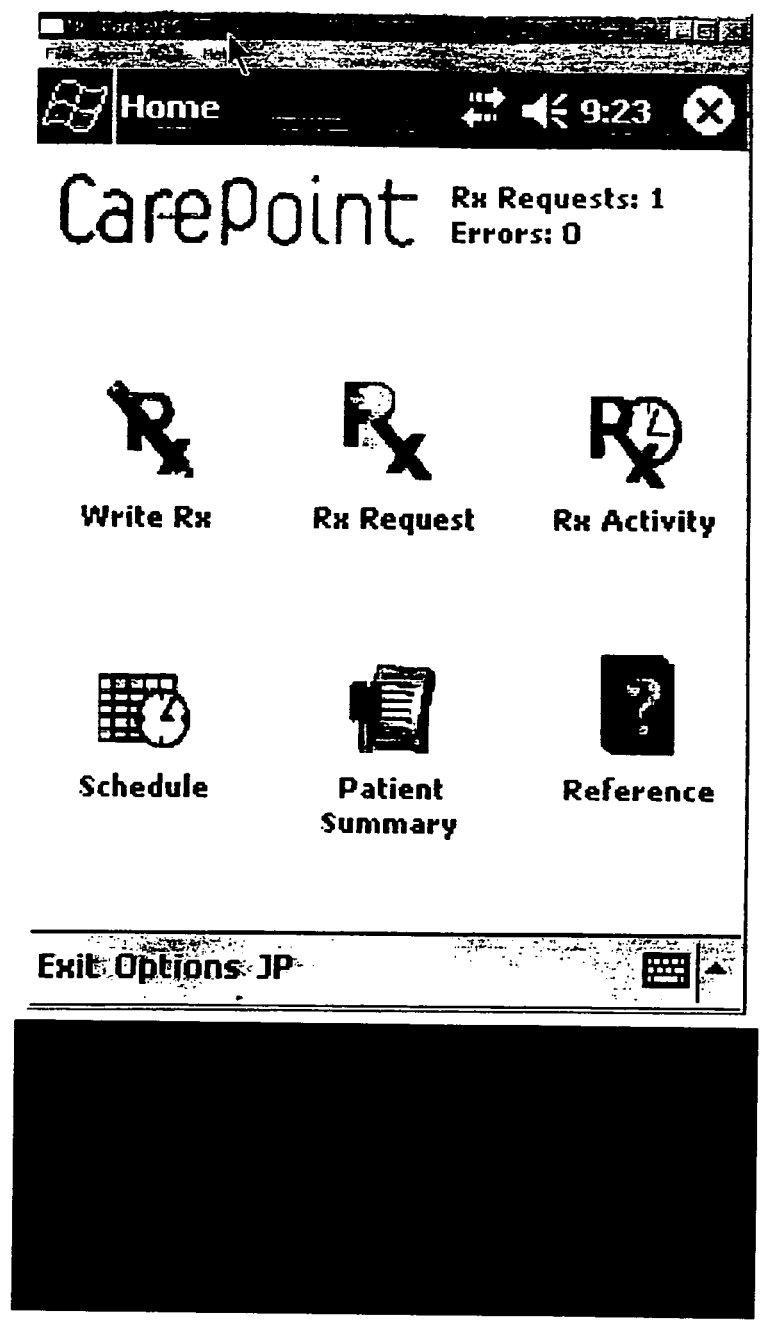
FIG. 7 is a menu user interface of a point of prescription application with icons for providing access to prescribing and alternative medication suggesting routines of the invention.
Figure 8:
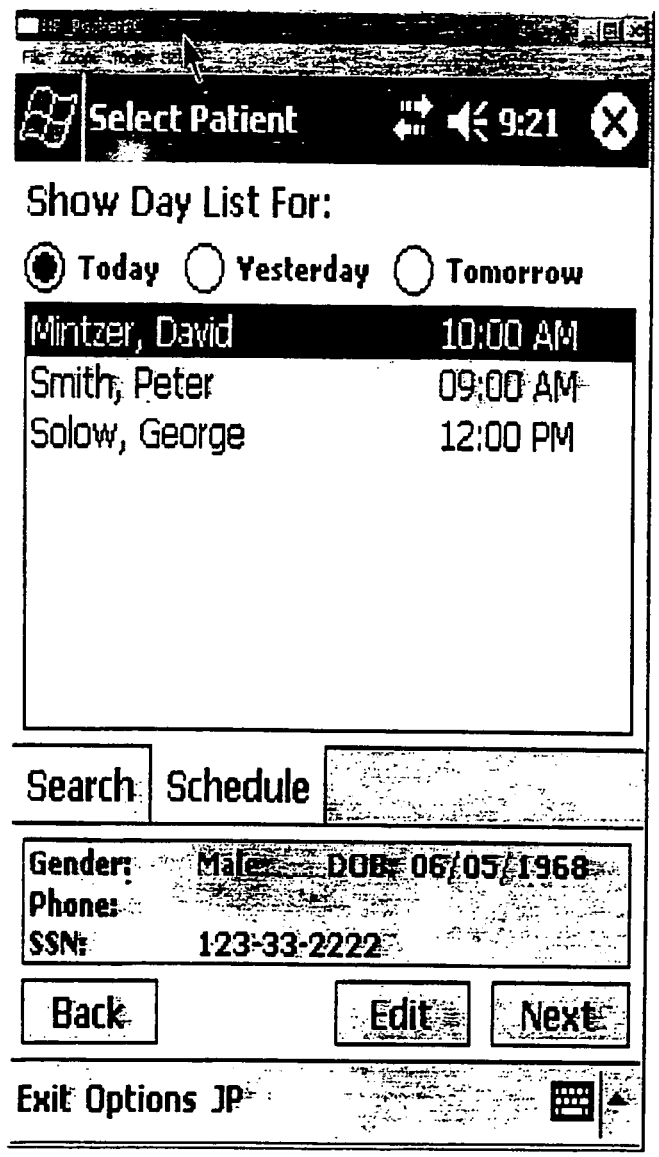
FIG. 8 is a patient list user interface of a point of prescription application for whom medications may be prescribed according to a selection of an alternative medication suggestion of the invention.
Figure 9:
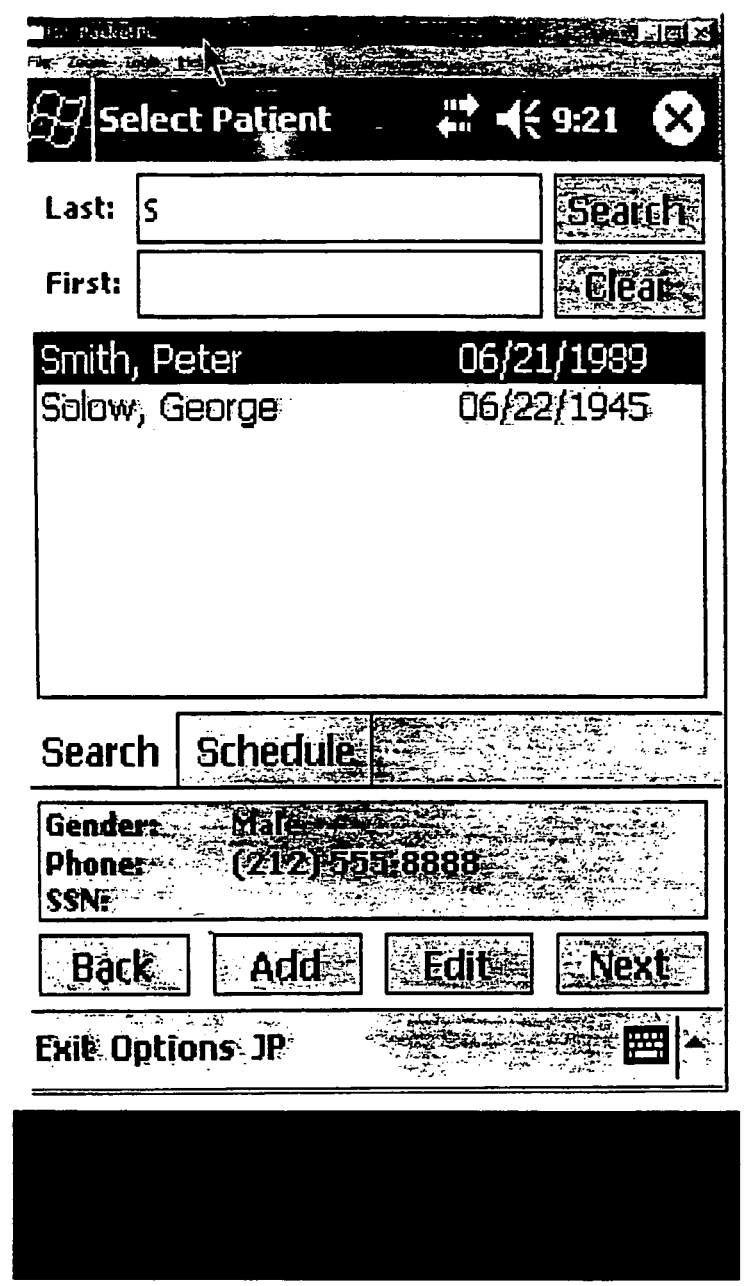
FIG. 9 is another patient list user interface of a point of prescription application for whom medications may be prescribed according to a selection of an alternative medication suggestion of the invention.
Figure 10:
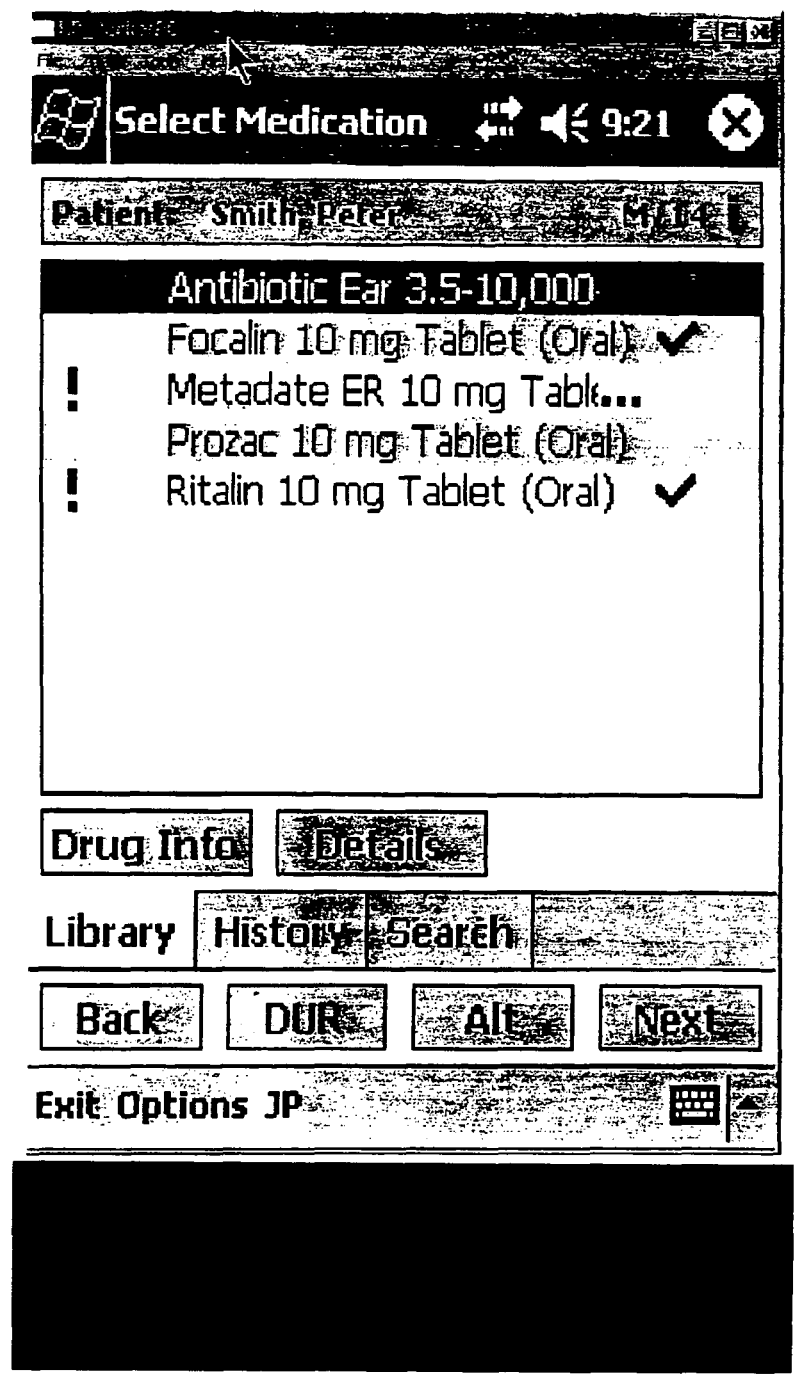
FIG. 10 is a prescription history list user interface showing various past prescriptions of a point of prescription application with action icons for performing DUR functions and accessing drug information.
Figure 11:
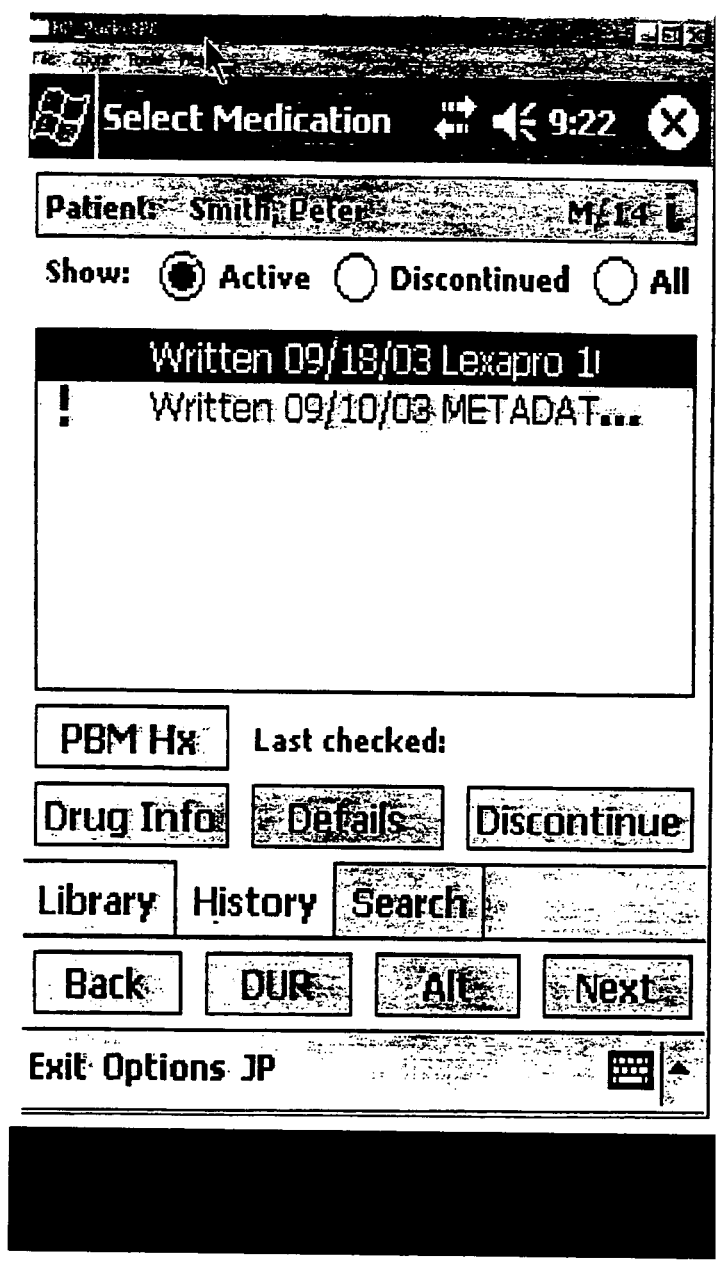
FIG. 11 is a prescription description user interface of a point of prescription application showing one prescription from the prescription history list of the user interface of FIG. 10 with action icons for performing DUR functions, accessing PBM history and requesting drug information.

The prescriber then may be prompted to select a schedule of patients by the appearance of a schedule icon (FIG. 7). With selection of the schedule icon, a patient list may be viewed for selection of a particular patient (FIG. 8 or 9). In general, access to the patient's medical history may be provided with this application on the prescribing device. Preferably, a list of medications is displayed for the patient as illustrated in FIG. 10. From such a list, the prescriber can select a medication that was prescribed to the patient, as in the example one that contains Prozac, and view related prescription information (e.g., date of prescription and prescribing doctor) (FIGS. 10 and 11). Such patient information may be accessed on the prescribing device 4, for example, as a patient and/or prescription information files. However, if not, such information may be requested from the physician database system 5, the prescription messaging data center 8, and/or the pharmacy system 12.

Figure 12:
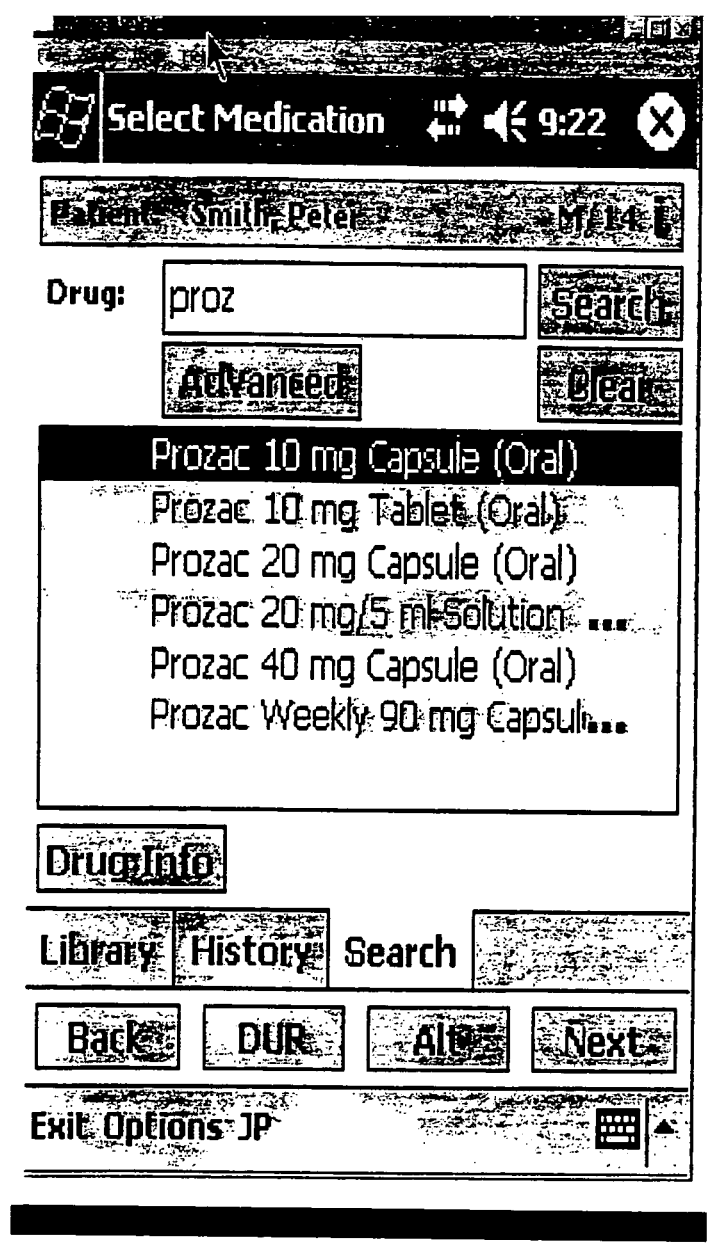
FIG. 12 is a search user interface of a point of prescription application for accessing information concerning particular brands of medications.
Figure 13:
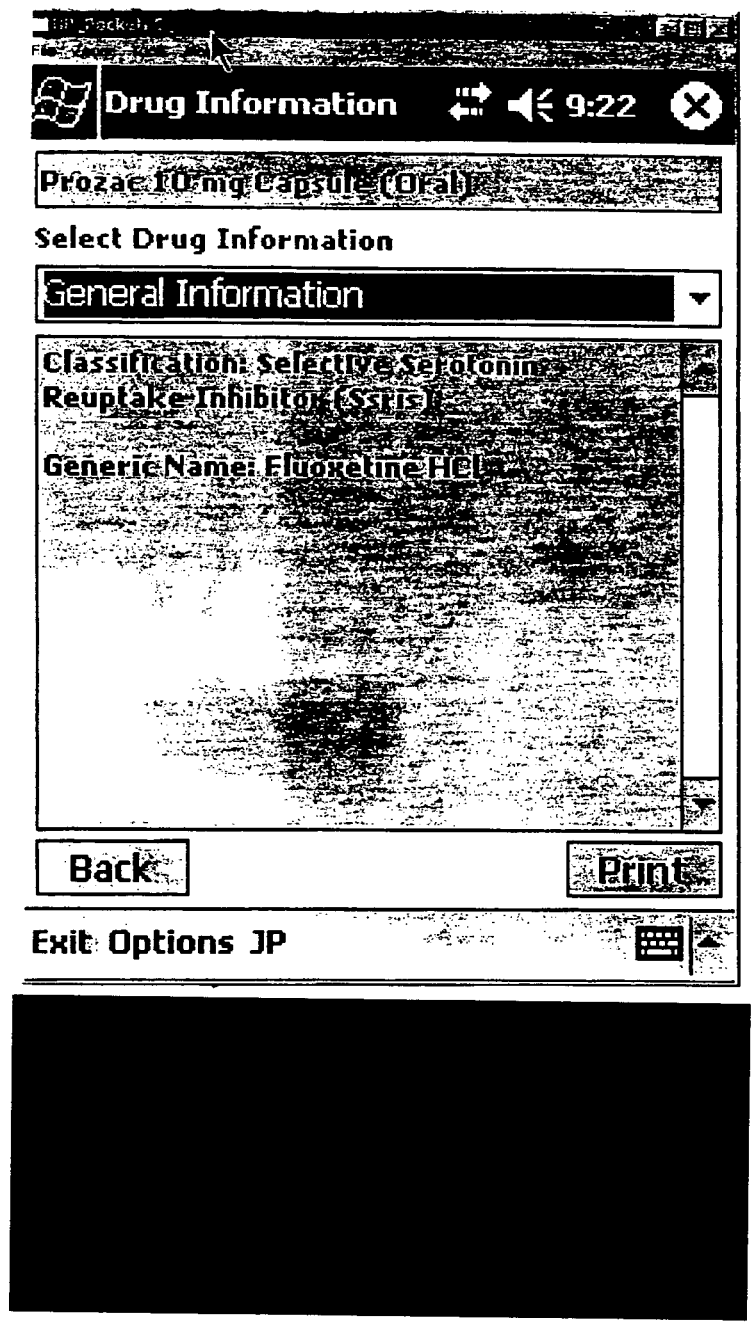
FIG. 13 is a drug information user interface of a point of prescription application for displaying information about a selected drug searched by the interface of FIG. 12.

As illustrated in FIG. 12 a list of available forms of the selected medication Prozac may be displayed. From the list, a specific medication may be selected (10 mg capsule oral). In further response to selection, drug information is displayed as illustrated in FIG. 13. Such drug information may be accessed on the prescribing device 4, for example, as drug information files. However, if not, such information may requested from the physician database system 5, the prescription messaging data center 8, the journal publishing system 13 and/or the pharmacy system 12.

Figure 13A:
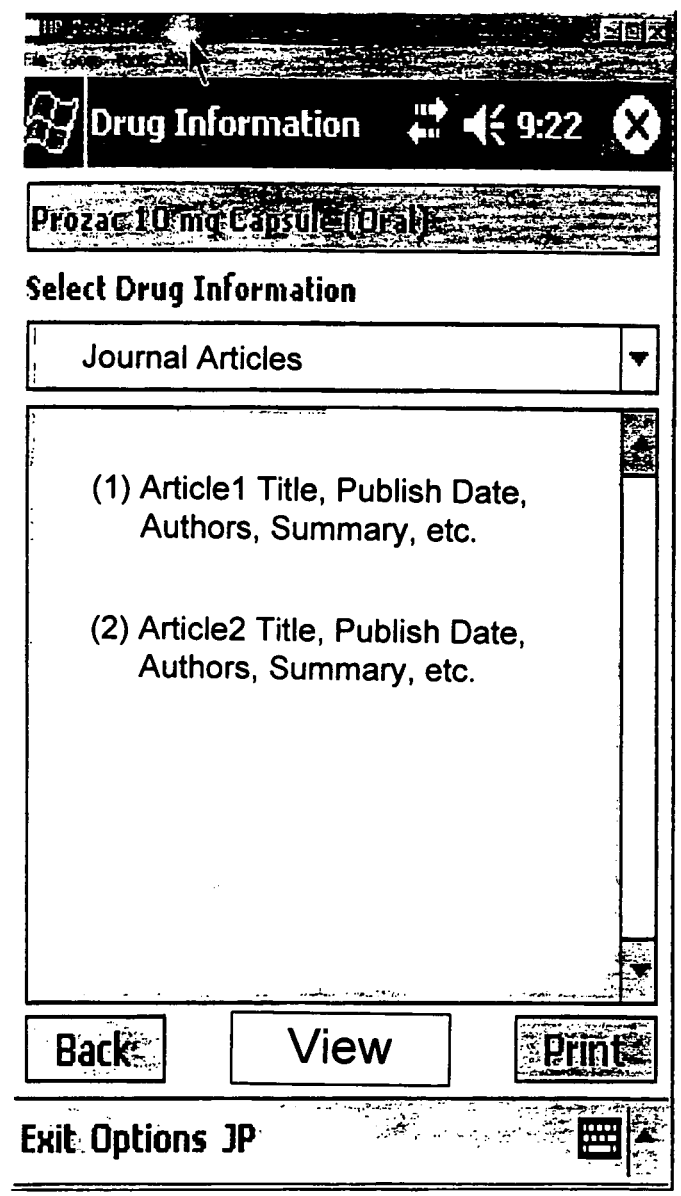
FIG. 13A is a drug information user interface of a point of prescription application for displaying, viewing or printing journal article information related to a selected drug searched by the interface of FIG. 12.

Optionally, as illustrated in FIG. 13A, such drug information may include a presentation of medical journal articles or medical journal publications related to the selected drug. For example, recent and/or historical reports or studies from medical journals or medical publications may be listed in response to a further selection by the prescriber of such information by the prescriber. Similarly, the prescriber may select a listed article from the list for viewing or printing an abstract, summary or the entire contents of the journal article. Thus, as illustrated in the figure, if the prescriber is interested in viewing articles about a medication, she may select a subtopic of "drug information", for example entitled "Journal Articles" that will provide the prescriber with access to medical journal articles or medical publication articles that may be related to prescribing the drug. In the event that the prescriber desires to access an article, the system or point of prescribing application may optionally be configured to process the request with information permitting payment for access to the article, such as, by forwarding credit card information or other authentication information such as username and password that permit the system to associate the journal access with a paid for or to be paid for journal access account. This account information may be maintained on any of the devices of the system and determined through communications over the network but preferably would be stored in the prescription messaging data center 8 and/or the journal publishing system 13.

Figure 14:
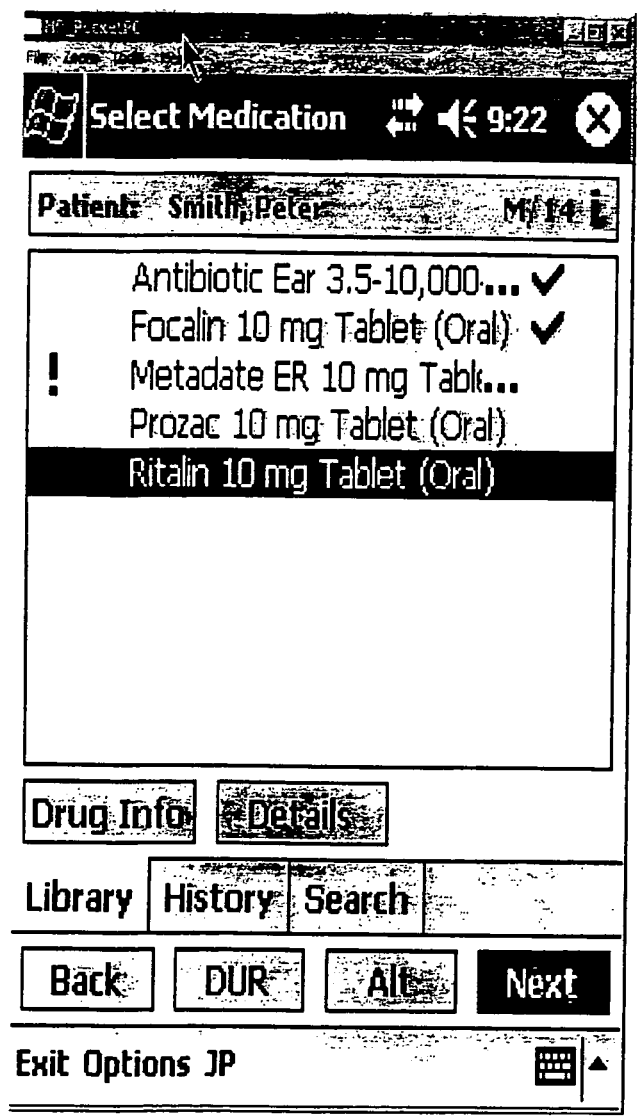
FIG. 14 is a medication selection user interface of a point of prescription application for selecting a medication to generate an electronic prescription for a patient.
Figure 15:
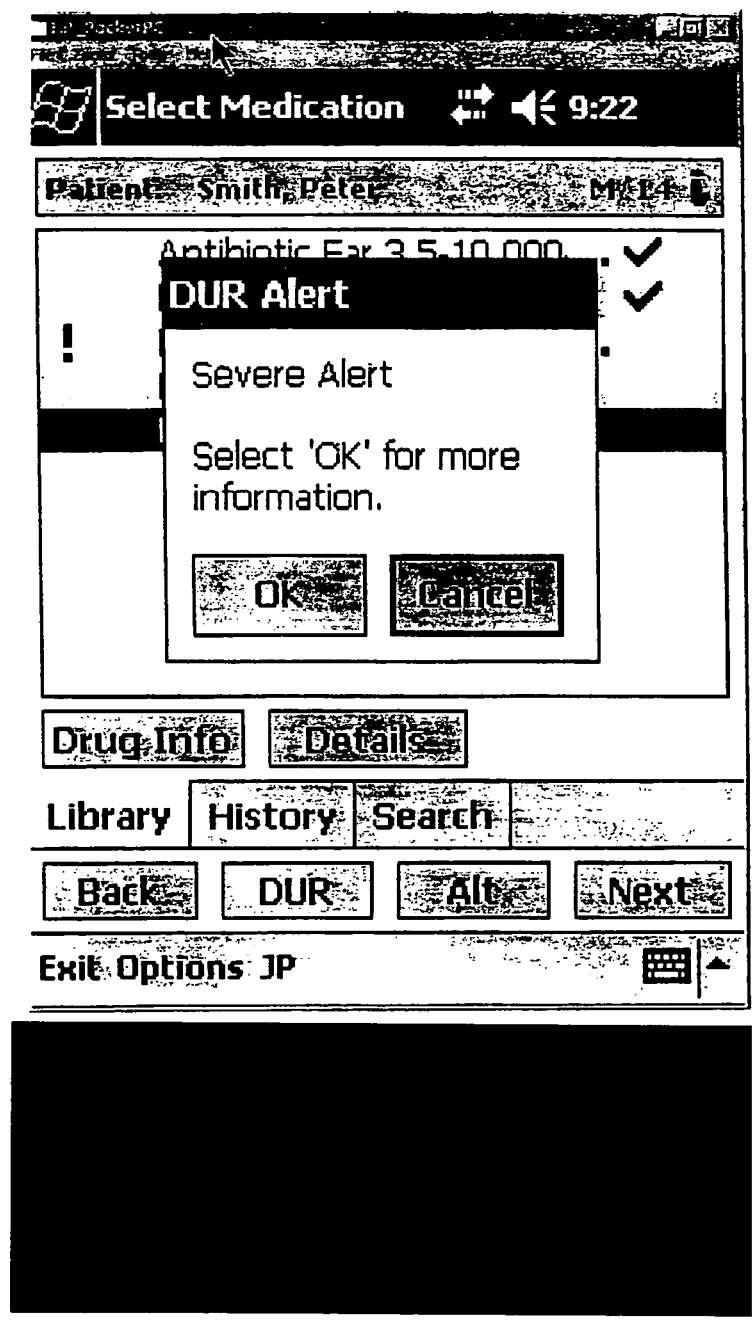
FIG. 15 illustrates an automated DUR alert from the user interface of FIG. 14 upon selection of a medication with the user interface of FIG. 14.
Figure 16:
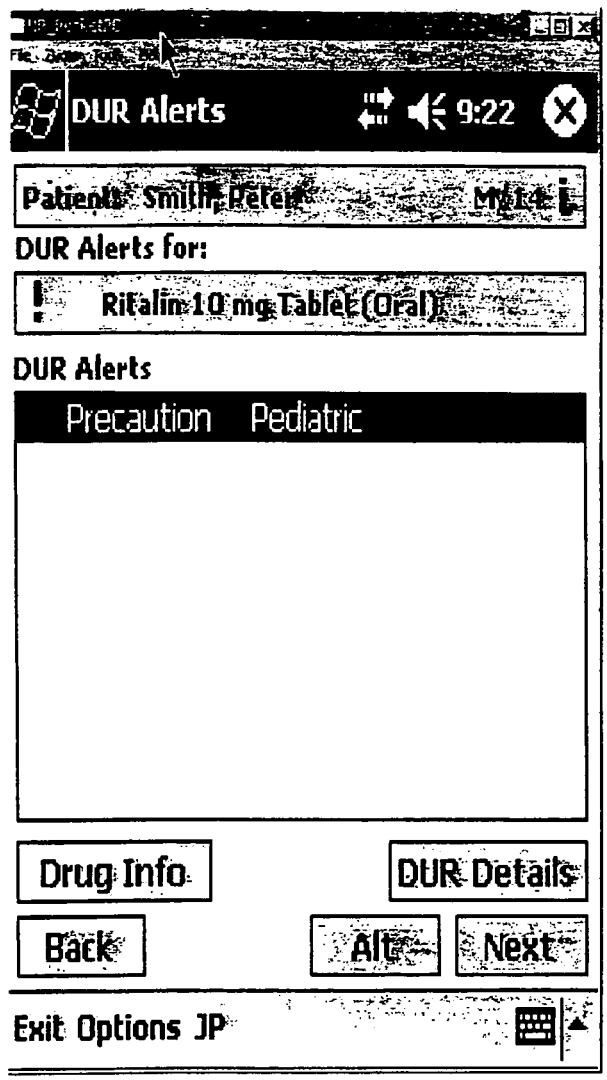
FIG. 16 illustrates presenting of further DUR information concerning the alert of FIG. 15 in the point of prescription application.
Figure 17:
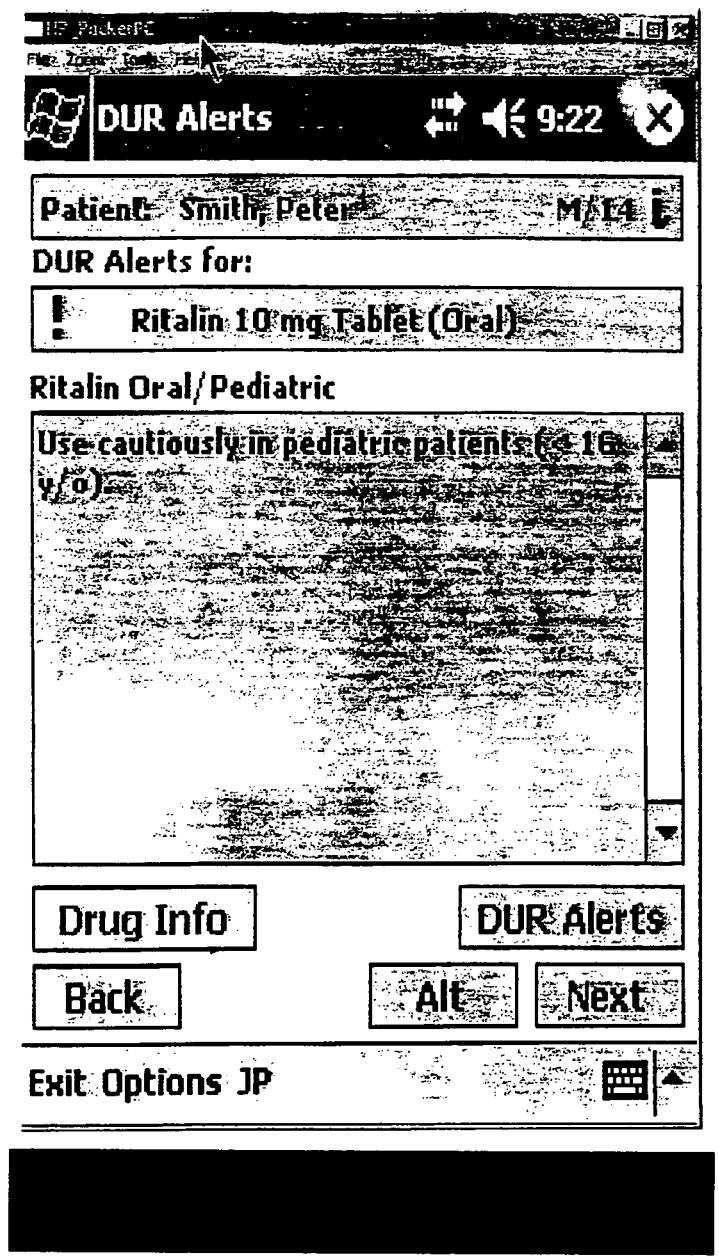
FIG. 17 illustrates presenting of still further DUR information concerning the alert of FIG. 15 in the point of prescription application.

The prescriber may also return to again view the list of medications for the patient as illustrated in FIG. 14. The prescriber then may select another medication, (e.g. Ritalin 10 mg). AS illustrated in FIG. 15, such selection may be followed by conducting a DUR ("drug utilization review") alert which is displayed if the prescriber proceeds in selecting that medication ("DUR Alert—Severe Alert"). Examples of such alerts are illustrated in FIGS. 15, 16 and 17. Of course, such an alert may be based on data currently or previously requested from a PBM over the network.

Additionally, the point of prescription messaging application 10 is configured with the control instructions for generating display of medication messages 21 suggesting one or more alternative medication(s) associated with a medication selection made on the prescribing device 4 or a medication message 21 suggesting a journal article or medical publication the prescriber may be interested in reading based on or associated with the selection of a particular drug. Alternative medication suggestions 20 may also be accompanied by a sponsor information message 22. Such messages may be based on data (e.g., associations between medications and (a) alternative medications from different sponsors, (b) sponsor messages and/or (c) journal messages) stored on the prescribing device 4 or transferred from prescription messaging data center 8 and/or journal publication system 13 as a result of a request based on the selection of the original medication or otherwise.

Figure 18:
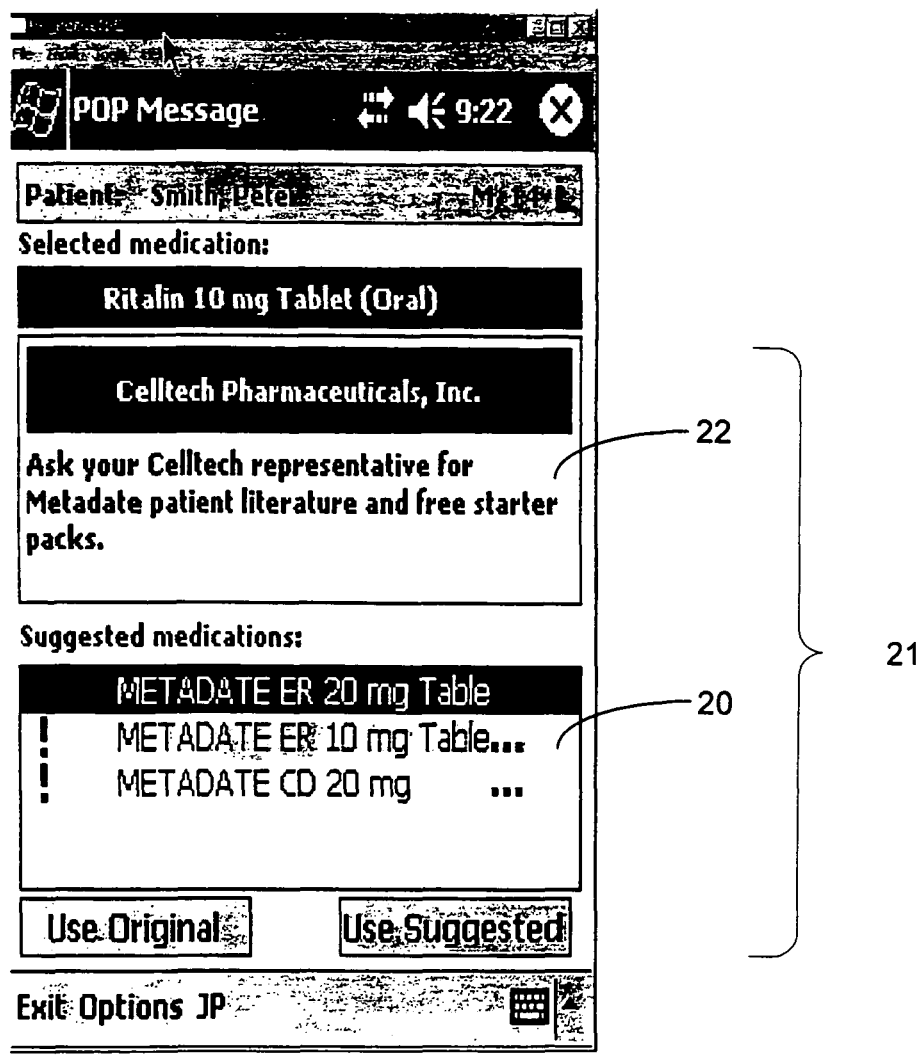
FIG. 18 illustrates a user interface of a point of prescription application with automated display of sponsor messages concerning alternative suggested medications associated with a selected medication, displayed in response to the selected medication, with action items for initiating functionality of selecting the original selected medication or a suggested alternative medication.
Figure 18A:
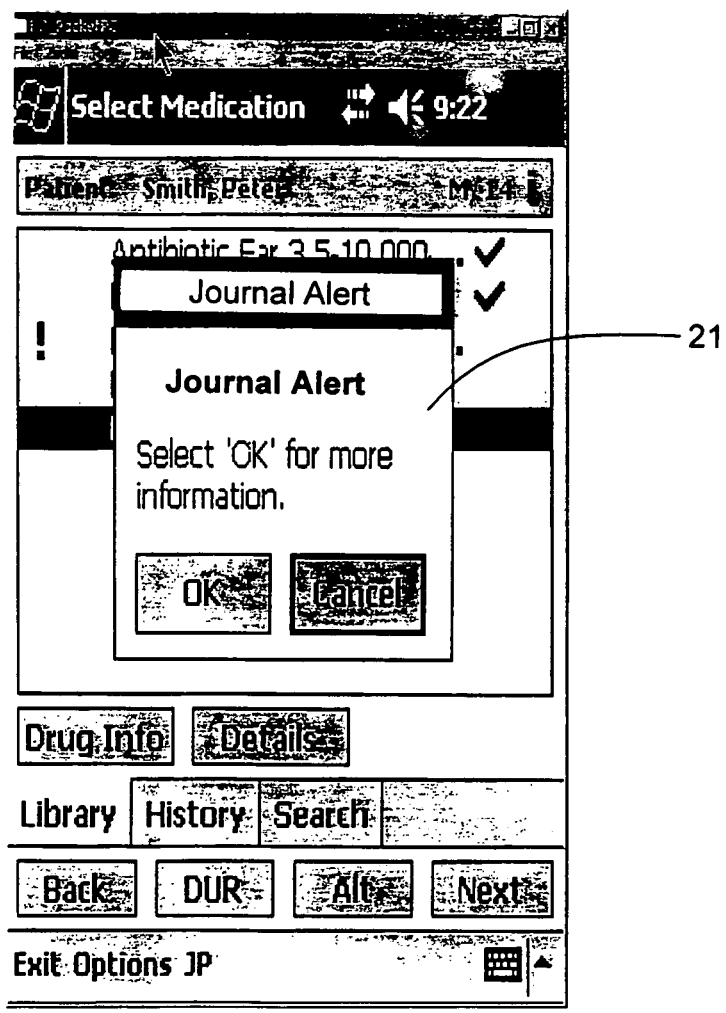
FIG. 18A illustrates an automated journal article alert from the user interface of FIG. 14 triggered upon prescriber's selection of a medication with the user interface of FIG. 14.

For example, as illustrated in FIG. 18A, if the prescriber proceeds or attempts to prescribe a medication for a patient, the prescribing device 4 may be configured to generate an automated message informing the prescriber of a particular journal article, such as, an article that may have been recently published in a journal that studies or describes the efficacy or possible problems recently discovered concerning the use the drug. This may provide a more proactive way to inform a physician about a particularly important medical journal or medical publication article as opposed to simply allowing the physician to search for additional drug information about a drug and then seeking out journal articles if he/she so desires as previously discussed with regard to FIG. 13A.

Figure 19:
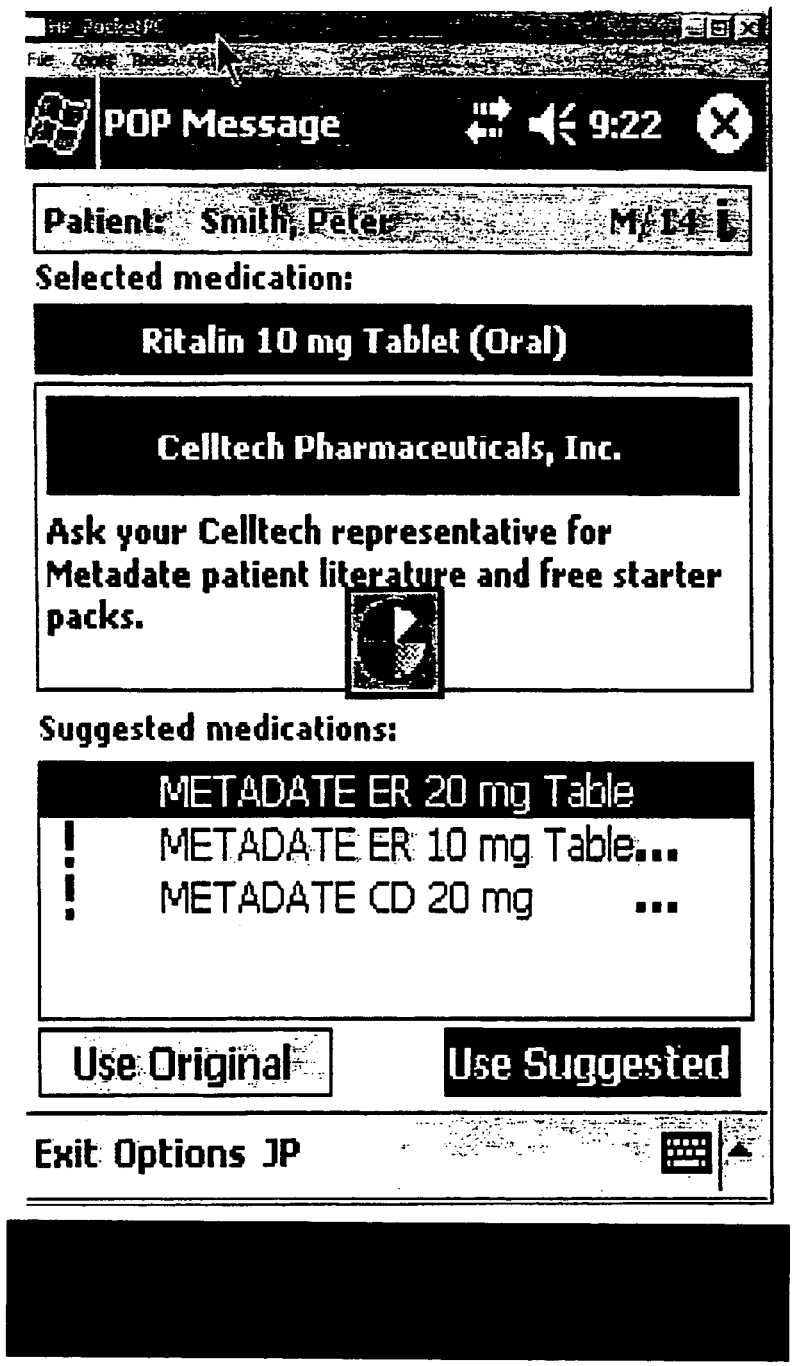
FIG. 19 illustrates selection of the action item initiating the functionality of selecting an alternative suggested medication in the user interface of a point of prescription application of FIG. 18.
Figure 20:
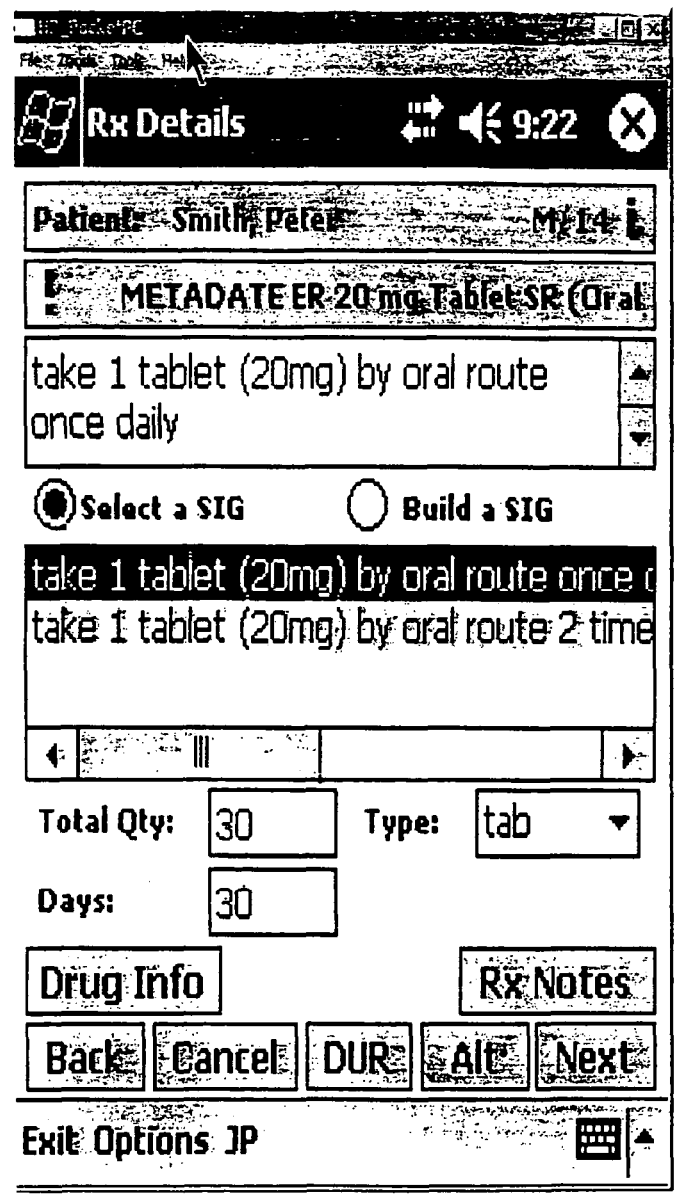
FIG. 20 illustrates a user interface of a point of prescription application showing further messages associated with the alternative suggested medication including several dose and usage instructions for the alternative suggested medication, also with action items for initiating of access to drug information for or performing a DUR with the alternative suggested medication.
Figure 21:
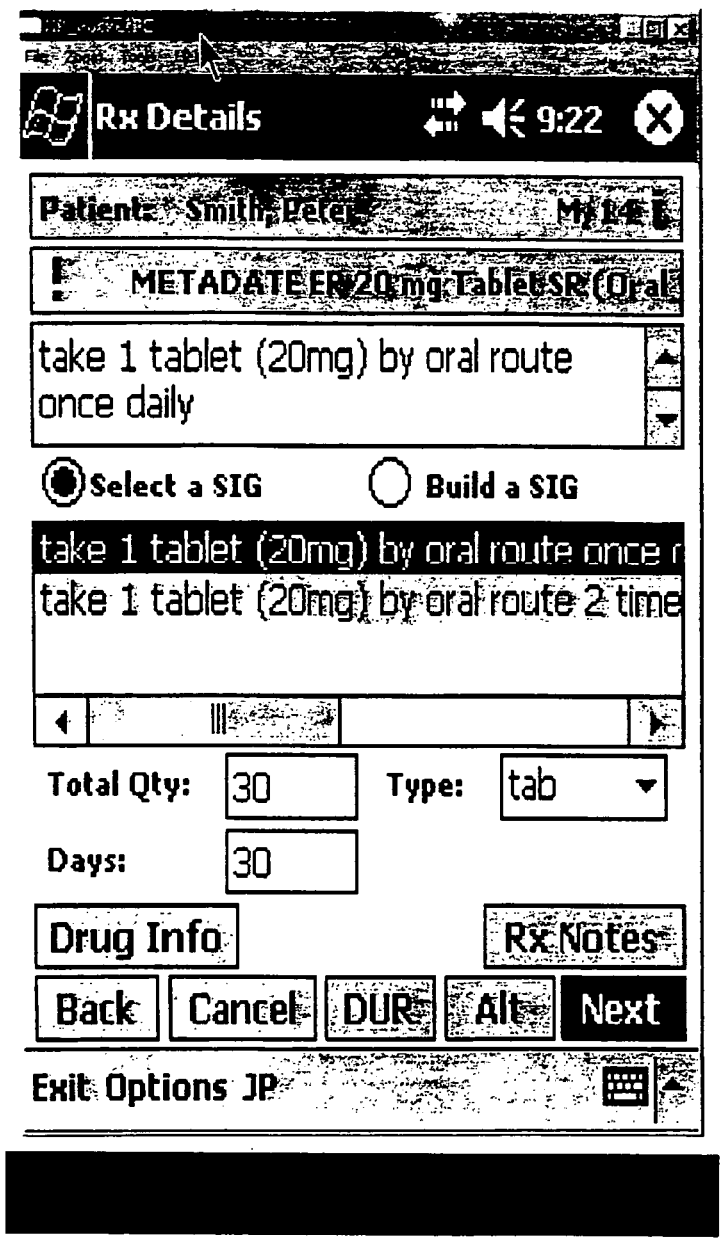
FIG. 21 is the user interface of FIG. 20, illustrates activation of a next icon for initiation functionality of completing selecting the alternative suggested medication with a default dose and usage instruction for an electronic prescription.

In the examples of automated messages illustrated in FIGS. 18 and 19, if the prescriber proceeds in selecting Ritalin, point of prescribing messages are displayed if that medication has an association with alternative medications of a different sponsor. Thus, alternative medication suggestions 20 sponsored by a maker of another medication may be displayed. The sponsor, seller or maker can define any number of such messages for one or more alternative medications. When such a message is launched, multiple messages can be cycled in the display of the prescribing device 4 according to a predetermined sequence such that a detailed presentation may be provided about the alternative medication.

In the illustrated example of FIG. 19, the messages are generated in response to Ritalin selection. In response, a different medication (e.g., Metadate) is suggested for treating the same condition in a suggested medication list. Moreover, an alternative medication message 22 suggesting the prescription of an alternative medication is displayed based on the prescriber selecting the particular medication. This message illustrates providing information to the prescriber on contacting the source of the alternative medication (e.g., the sponsor, seller or maker of the alternative medication), for example, to find out information about the medication. The message may also suggest one or more "SIG"(s) (i.e., doses and/or usage instructions related to prescribing the alternative suggested medication (e.g., "take one tablet (20 mg) by oral route once a day before bedtime"). Such dose and usage instruction messages are illustrated in the user interface of FIG. 20. The prescriber may select a suggested dose and usage instruction, use a default suggested dose and usage instruction or create a custom one that can then be incorporated into a prescription. Optionally, the alternative medication may be accompanied by a link to a journal article or publication about the alternative medication, for example, a journal article which describes the use of the alternative medication as an alternative to the selected mediation.

Stating this another way, the originally selected medication provides a 'trigger' for displaying a message suggesting an alternative 'target' medication or displaying a journal article or medical publication. While alternative medications or messages of a sponsor common to the trigger medication may be displayed, the display of messages suggesting the alternative medication is typically based on the suggested medications of a different sponsor or maker. Such messages offer a way for sponsored promotion of other brand name medications to the prescriber as an alternative to the selected brand name or generic medication at the point of prescription.

Typically, an electronically stored table or other database type data structure is used to relate or associate the trigger medications to target medications and/or journal articles or medical publications. Preferably, information about each medication is stored and displayed by a drug name, a strength, a dose form, and a route of administration (e.g., Ritalin 10 mg Tablet (Oral)). Of course, complete medical information concerning the drug may also be accessed or view with the prescribing device 4. When the prescriber selects a medication on the prescribing device, the table is consulted electronically in response thereto either locally or via communications such as over the network 6. If the medication is a trigger medication, a message suggesting the target medication and/or target journal article is/are then displayed.

One such table is shown for purposes of illustration in FIG. 23. Those skilled in the art will recognize other data structures and programming techniques for implementing a display of messages based on alternative medication suggestions as discussed herein. In the illustrated table, selected Medication-A offered or made by Sponsor-A has six possible alternatives associated with it. These include Medication-B, Medication-BB, Medication-BBB, each from Sponsor B. Alternative medications labeled Medication-C and Medication-CC are sponsored by different Sponsor-C and are also associated as alternatives of Medication-A. Finally, alternative Medication-AA of Sponsor A is also an alternative of Medication-A. Such alternatives and their associations as represented by the table structure would be previously determined based on the medical information associated with the medications if such medications are equivalently used for a particular patient diagnosis such that either one may be selected. However, such associations need not strictly be intended for alternative use but may indicate use in conjunction with the originally selected medication to the extent that they relate to a common patient diagnosis. Optionally, the associations may simply be based on associations specified by a particular sponsor, maker or seller of such targeted medications without relation as an alternative drug equivalence or any relationship to a given diagnosis for a patient.

In a preferred embodiment, the table optionally includes additional data condition(s) (one or more) that help to determine whether any alternatives will be displayed in response to the medication selection and the content of such message. Thus, in response to the selection, the table is checked to determine if one or more alternative medications should be displayed based on the association between the trigger and target medications as well as any additional preset condition(s). For example, the table may include conditions based on the age and/or gender of the patient. In such a case, when the trigger medication is selected by the prescriber, the particular target medication displayed can differ based on the patient's age and/or gender.

An example of such a table is illustrated in FIG. 24 with sample conditions based on age and gender. Thus, for a female patient based on the existing hypothetical table example, if a Medication-A is selected, Medication-C would not be suggested. If the female patient was over 18 years of age, Medication-BB would also not be suggested. Thus, for this patient, of the six associated medications, only the remaining four would be displayed (i.e., Medication-B, Medication-BBB, Medication-CC, and Medication-AA).

Other embodiments of the system may include other conditions or factors controlling the display of alternative suggested medications (targets). For example, display of a particular message or suggestion of a particular target medication can be conditioned on the location of the prescriber or patient, e.g., location within a particular region of the United States such as Northeast, Southeast, Midwest, state, county, town, etc. Thus, for the above example, if the female, over 18 patient was in a Northern region, upon selection of Medication-A, Medication-C and Medication-CC would be excluded. Thus, only Medication-B and Medication-BBB would be displayed as suggested alternatives.

Finally, a date condition may also be applied, for example, based on when an insurance plan, sponsor or maker intends to phase out or phase in a medication. Similarly, such a date filter may simply relate to a particular period of time that a sponsor desires to have its medications suggested as alternatives. Thus, with regard to additionally applying a date filter or condition to the above example, if the selection by the prescriber was being made for after Jan. 1, 2001, Medication-BBB would be excluded and only Medication-B would be suggested as the target for the prescriber's selection of Medication-A.

In the case where target medical journal messages are stored in the prescribing device 4 or prescription messaging data center 8, such stored data may include title, publication date, authors and an abstract or summary and optionally the full text and/or images of the article. In such a case where only an abstract or summary is stored, it is preferred to also include a data link to the source of the complete article in the journal publishing system 13 for download, printing, viewing, purchase, etc. by the prescriber preferably on or from the prescribing device.

A table illustrating the storage of such a journal article in association with a trigger medication is illustrated in FIG. 25. As illustrated in the table, information pertaining to journal article or medical publication "Article1" would automatically be presented in an alert to the prescriber on the prescribing device 4 in response to a selection of medication—A in conjunction with suggesting alternative medication—BBB regardless of the journal article's publication date. "Article2" would automatically be presented in an alert to the prescriber on the prescribing device 4 in response to a selection of medication—AA regardless of the article's publication date. "Article3" would automatically be presented in an alert to the prescriber on the prescribing device 4 in response to a selection of Medication—AAA, if the selection of Medication—AAA was no later than 30 days past the publication date of the journal article.

In these ways, the display of alternative suggested medications or journal articles may be filtered by various conditions to save the physician time from viewing an unrelated or outdated journal article or selecting a suggested medication for the patient that would not be appropriate and would have to be subsequently changed after it is discovered that it was an inappropriate selection for any given reason. The system may also be implemented to maximize the presenting of education information pursuant to a desired set of conditions specified or desired by a sponsor. While the illustrated filtering conditions of FIG. 24 and FIG. 25 include age, gender, region and date, other conditions for filtering suggested medications, for example, such as a sponsor or maker condition, may be implemented. Thus, the application may control restricting any sponsor from designating a trigger medication for more than one group of target medications or only the display of a single sponsor's alternative medication suggestions may be implemented. Similarly, the same medication may be controlled such that it cannot be a trigger for more than one sponsor in any designated region.

Optionally, additional control conditions or rules for displaying associated alternative medications or journal articles may include a set maximum number of times to show messages to a particular physician for a group of target or trigger medications. The application may also control how frequently to trigger a message. For example, the message for any given alternative or article may be shown every time a trigger medication is selected, every other time, every third time, only the first time, etc. Preferably, a message will not be triggered more than once for a single prescription.

Furthermore, such conditions in determining whether the display of a journal article, target or alternative medication in response to selection of a trigger medication may additionally be based on other patient information such as first, second, third, etc. diagnoses data of the patient such as if the target medication or article would be inappropriate or appropriate for consideration with respect to one or more of such diagnoses which may or may not be common with a diagnosis for which the trigger medication was selected. For example, medication or drug related data with regard to the particular diagnoses for which the suggested medication is prescribable would be compared to the patient's actual diagnoses.

In an example of such a system, one or more journal articles may be related to or associated with one or more patient diagnoses or treatments rather than or in addition to the trigger medication. In this event, the journal article may be displayed as a result of the determination that patient for which a prescriber is prescribing a drug has the associated diagnosis or treatment. In such a situation where a diagnosis and/or treatment is the trigger, the point of prescription application 10 may display an option to the prescriber to review medical journal articles related to the treatment(s) or diagnoses when a patient is selected such that the application accesses patient diagnosis and treatment information in response to the patient selection. This selection then initiates a comparison of the table or other data structure(s) based on one or more of the patient's diagnoses or treatments and will result in selection of related article(s) of the table or data structure for presenting to the prescriber to review or purchase.

Subsequently, with the presented alternative suggested medication and/or journal article information, filtered by these conditions or otherwise, the prescriber may choose to prescribe a presented target medication. This selected medication, as with the original trigger medication, may also be automatically subjected to an electronic DUR for checking for conflicts with the patient's history or the patient's insurance plan on the prescribing device 4 and informing the physician of the results. In this event, patient name, social security data, address or other patient identifier information may be used when checking the medication. However, the DUR and formulary requirements may also alternatively be implemented as conditions restricting the display of an alternative medication suggestion or target medication if it would not satisfy the DUR or formulary restrictions of the patient and plan, thus, preventing the prescriber from reviewing the suggested medication if it did not satisfy the DUR and formulary requirements. This may be achieved by automated remote access to PBM information over the network 6 or by automated access to previously stored information on the prescribing device 4.

Figure 22:
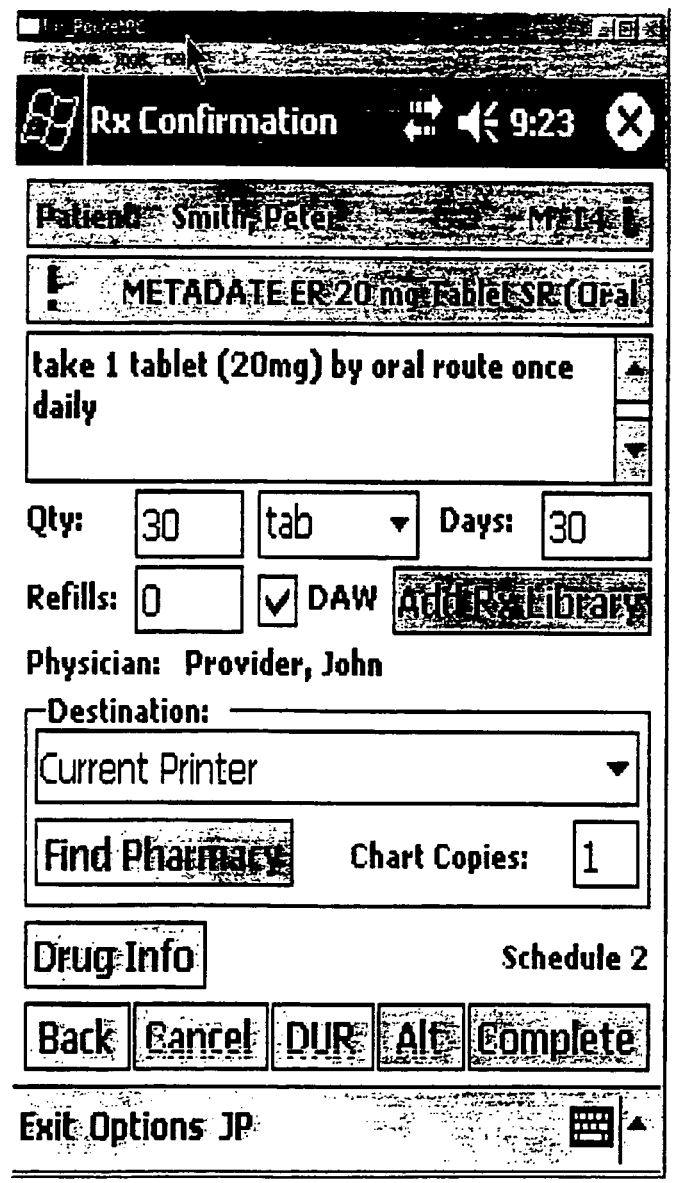
FIG. 22 is a user interface of a point of prescription application in response to the selection from the user interface of FIG. 21, displaying action items for finalizing an electronic prescription.

Of course, the prescriber may disregard the alternatives suggested and prescribe the original selected trigger drug. The prescriber may even delete or cancel the selected original drug, select a presented alternative target medication which is not equivalent to the original as well as selecting another alternative target medication which is equivalent to the original selected medication. As illustrated in the example shown in FIGS. 19, 20 and 21, upon selecting the alternative suggested medication and the prescriber may proceed to generate an electronic prescription. As illustrated in FIG. 22, the prescription process may be completed by using the application to initiate a transfer of the created electronic prescription to a pharmacy system 12 over the network 6.

Thus, the resulting prescriptions are automatically sent to a patient's pharmacy with a simple click of a button via secure communication such as via a fax telephone line. Prescriptions can also be printed for chart copies or for patients. Because the prescriber's signature is captured at the session login, it can appear on all prescription scripts written during that session.

Optionally, the point of prescription messaging application 10 may also control tracking of information associated with targeted medication suggestions. For example, for each physician in a practice or based on a group of physicians of a practice, the application can record the number of times a message was triggered for any targeted medications. For prescribed targeted medications, it may also record whether or not the target medication was chosen as a result or in connection with the display of a triggered message, and, if so, which message was displayed. This tracking of data may also include monitoring of which medication was originally chosen, as well as the DUR and formulary status of both the original triggered medication and the target medication for purposes of future comparison.

In one embodiment, the system or point of prescription messaging application 10 may configured to generally track or search the medical treatment and/or diagnosis information of the patients of the prescriber and offer access to related articles at a predetermined point of the prescription application, such as, after logging into the point of prescription application 10. In this example, articles may be offered to the prescriber and optionally organized based on the diagnosis or treatment information (e.g. drug) of which the article has been associated. Thus, medical journal publication articles may be listed with a diagnosis identifier and other such articles may be listed by a treatment or drug identifier to indicate their association. By such tracking or monitoring or otherwise presenting related or associated articles, physicians can be provided with medical journal article offers particularly based on their prescribing patterns and specific patient needs.

As discussed herein, the tables or data structures for identifying articles may be created by searching text of medical journal articles and generating a table with key drug, treatment or diagnosis terms from the article(s). Other associations may also be chosen manually.

With the various embodiments of the system, sponsors can benefit from providing targeted messages that offer alternative drugs at the point of prescribing. Physicians and patients benefit when the prescriber or physician selects a designated trigger medication because a sponsor-defined point-of-prescribing message is displayed that will identify the sponsor and educate the physician on one or more beneficial alternatives to the medication selected. Physicians, and ultimately their patients, also can benefit by having greater access to immediately pertinent educational information.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method comprising:
   prompting, via a user interface, a prescriber to enter an electronic handwriting sample;
   receiving the electronic handwriting sample within a signature input user interface;
   synchronizing, via an encrypted communication interface and at a device, information relating to a patient that is stored in a physician-accessible database with information relating to the patient that is stored in a pharmacy database implemented by multiple servers accessible over secure networks and equipped with one or more communications devices for communication with one or more prescribing devices having point of prescription applications, and including processor control instructions for communications between the prescribing devices for prescription related data exchange;
   receiving, in relation to a diagnosis and via the device, a prescription input;
   receiving, via the user interface, an input that authorizes electronic prescribing of a medication associated with the prescription input;
   receiving, from a sponsor and in relation to the first medication, one or more publication data items that are associated with the second medication in relation to a prescribing pattern of a plurality of prescribers;
   receiving, from the sponsor, one or more display conditions that restrict presentation of the one or more publication data items in relation to the prescribing pattern of the plurality of prescribers;
   receiving, at the device, via a first icon presented at a first user interface for accepting selections for inclusion in an electronic prescription and in relation to the diagnosis, a selection of a second medication;
   determining that the first medication is an alternative to the second medication;
   identifying by a messaging controller and based on the selection of the second medication of the second medication by the one of the plurality of prescribers, the prescribing pattern of the plurality of prescribers in relation to the at least one of a first medication or the second medication and the selection of the second medication by the one of the plurality of prescribers in relation to the first patient in relation to the diagnosis and in relation to the prescribing pattern of the plurality of prescribers, at least one of the one or more publication data items that identifies, in relation to the diagnosis, one or more problems associated with a use of the second medication in relation to the diagnosis;
   generating, by a prescription messaging data center server and based on an identification of the at least one of the one or more publication data items, an alert, the alert comprising (a) a link to the at least one of the one or more publication data items that identifies, in relation to the diagnosis, the first medication as an alternative to the second medication, and (b) an option to select the first medication in lieu of the second medication, wherein the at least one of the one or more publication data items is organized in relation to the diagnosis;
   providing the alert via a second user interface and in relation to the second medication in relation to a diagnosis and a determination that the one or more conditions received from the sponsor are met;

generating an electronic prescription pertaining the second medication; and initiating an automatic transfer of the generated electronic prescription to a pharmacy system via a secure communication interface.

2. The method of claim 1 further comprising automatically displaying,
in response to a selection by the one of the plurality of prescribers and via a messaging controller, the at least one of the one or more publication data items.

3. The method of claim 1 wherein the at least one of the one or more publication data items comprises title information.

4. The method of claim 1 wherein determining, based on one or more associations between the second medication and the first medication, that the first medication is an alternative to the second medication comprises determining based on treatment information associated with the second medication that the first medication is an alternative to the second medication.

5. The method of claim 1 wherein determining, based on one or more associations between the second medication and the first medication, that the first medication is an alternative to the second medication comprises determining based on drug information associated with the second medication that the first medication is an alternative to the second medication.

6. The method of claim 1 wherein determining, based on one or more associations between the second medication and the first medication, that the first medication is an alternative to the second medication comprises determining based on diagnosis information associated with the second medication that the first medication is an alternative to the second medication.

7. The method of claim 6 wherein identifying the at least one of the one or more publication data items comprises identifying the at least one of the one or more publication data items in response to a selection of the diagnosis information.

8. The method of claim 1 further comprising generating, an order for further publication data items.

9. The method of claim 8 further comprising displaying the further publication data items after generating the order, wherein the further publication data items comprise text of a medical journal article.

10. The method of claim 1 further comprising processing at least one of the first medication or the second medication for distribution to a patient.

11. A method comprising:
prompting, via a user interface, a prescriber to enter an electronic handwriting sample;
receiving the electronic handwriting sample within a signature input user interface;
synchronizing, via an encrypted communication interface and at a device, information relating to a patient that is stored in a physician-accessible database with information relating to the patient that is stored in a pharmacy database implemented by multiple servers accessible over secure networks and equipped with one or more communications devices for communication with one or more prescribing devices having point of prescription applications, and including processor control instructions for communications between the prescribing devices for prescription related data exchange;
receiving, in relation to at least one of a first medication or a second medication and via the device, a prescription input;

receiving, via the user interface, an input that authorizes electronic prescribing of a medication associated with the prescription input;
receiving, from a sponsor and in relation to the first medication, one or more publication data items that are associated with the second medication in relation to a prescribing pattern of a plurality of prescribers;
receiving, from the sponsor, one or more display conditions that restrict presentation of the one or more publication data items in relation to the prescribing pattern of the plurality of prescribers;
receiving at a prescribing device, via a user interface and in relation to a first patient, a selection of the second medication;
determining, based on one or more associations between the second medication and the first medication, that the first medication is an alternative to the second medication;
identifying by a messaging controller and based on the selection of the second medication by the one of the plurality of prescribers, the prescribing pattern of the plurality of prescribers in relation to the at least one of a first medication or the second medication and the selection of the second medication by the one of the plurality of prescribers in relation to the first patient in relation to the diagnosis and in relation to the prescribing pattern of the plurality of prescribers, at least one of the one or more publication data items that identifies, in relation to the diagnosis, one or more problems associated with a use of the second medication in relation to the diagnosis;
generating, based on an identification of the at least one of the one or more publication data items, an alert, the alert comprising (a) a link to the at least one of the one or more publication data items that identifies the first medication as an alternative to the second medication, and (b) an option to select the first medication in lieu of the second medication, wherein the at least one of the one or more publication data items is organized in relation to the diagnosis;
providing the alert to the one of the plurality of prescribers in relation to a second patient associated with the diagnosis in view of a determination that the one or more conditions received from the sponsor are met;
generating an electronic prescription pertaining the second medication; and
initiating an automatic transfer of the generated electronic prescription to a pharmacy system via a secure communication interface.

12. The method of claim 11 further comprising receiving requests comprising one or more medications and sending responses comprising publication data items.

13. The method of claim 12, wherein the publication data items comprise text of a medical journal article.

14. The method of claim 11 wherein the publication data items comprise title information.

15. The method of claim 11 wherein determining, based on one or more associations between the second medication and the first medication, that the first medication is an alternative to the second medication comprises determining based on treatment information associated with the second medication that the first medication is an alternative to the second medication.

16. The method of claim 11 wherein determining, based on one or more associations between the second medication and the first medication, that the first medication is an alternative to the second medication comprises determining based on drug information associated with the second medication that the first medication is an alternative to the second medication.

17. The method of claim 16, further comprising controlling requesting of publication data items in response to receipt of the selection.

18. The method of claim 11 further comprising controlling requesting of publication data items in response to receipt of the selection.

19. The method of claim 11, further comprising transmitting an electronic prescription.

20. The method of claim 11, wherein providing the alert to the one of the plurality of prescribers in relation to a second patient associated with the diagnosis comprises providing the alert to the one of the plurality of prescribers in relation to a second patient associated with the diagnosis prior to receiving a selection of a medication in relation to the second patient.

21. A system comprising:
a memory; and
a processor, coupled to the memory and configured to:
prompt, via a user interface, a prescriber to enter an electronic handwriting sample;
receive the electronic handwriting sample within a signature input user interface;
synchronize, via an encrypted communication interface and at a device, information relating to a patient that is stored in a physician-accessible database with information relating to the patient that is stored in a pharmacy database implemented by multiple servers accessible over secure networks and equipped with one or more communications devices for communication with one or more prescribing devices having point of prescription applications, and including processor control instructions for communications between the prescribing devices for prescription related data exchange;
receive, in relation to a diagnosis, and via the device, a prescription input;
receive via the user interface, an input that authorizes electronic prescribing of a medication associated with the prescription input;
receive, from a journal publishing system, and in relation to the first medication, one or more publication data items that are associated with the second medication in relation to the prescribing pattern of the plurality of prescribers;
receive, from a sponsor, one or more conditions for providing the one or more publication data items in relation to a prescribing pattern of a plurality of prescribers;
receive at the device, via a user interface and in relation to the diagnosis, a selection of a second medication;
determine in relation to the diagnosis, that the first medication is an alternative medication to the second medication;
identify, by a messaging controller and based on the selection of the second medication by the one of the plurality of prescribers, the prescribing pattern of the plurality of prescribers in relation to the at least one of a first medication or the second medication and the selection of the second medication by the one of the plurality of prescribers in relation to the first patient in relation to the diagnosis and in relation to the prescribing pattern of the plurality of prescribers, at least one of the one or more publication data items that identifies, in relation to the diagnosis, one or more problems associated with a use of the second medication in relation to the diagnosis;
generate, based on an identification of the at least one of the one or more publication data items, an alert, the alert comprising (a) a link to the at least one of the one or more publication data items that identifies, in relation to the diagnosis, the first medication as an alternative to the second medication, and (b) an option to select the first medication in lieu of the second medication, wherein the at least one of the one or more publication data items is organized in relation to the diagnosis;
provide, in view of a determination that the one or more conditions received from the sponsor are met, the alert in relation to the second medication;
generate an electronic prescription pertaining the second medication; and
initiate an automatic transfer of the generated electronic prescription to a pharmacy system via a secure communication interface.

22. The system of claim 21, wherein the processor is further configured to access a data structure that relates medications and publication information.

23. The system of claim 22, wherein the processor is further configured to generate charge information associated with ordering publication data items, wherein the publication data items comprise text of a medical journal article.

24. The system of claim 21, wherein the processor is further configured to provide the at least one of the one or more publication data items based on a selection of the second medication identifier.

25. The system of claim 21, wherein the processor is further configured to display medical journal publication information.

26. The system of claim 21, wherein the processor is further configured to display medical journal publication information based on a treatment.

27. The system of claim 21, wherein the processor is further configured to display medical journal publication information in response to a selection of a patient.

28. A non-transitory computer-readable medium having instructions stored thereon that, when executed by a processor, cause the processor to perform operations comprising:
prompting, via a user interface, a prescriber to enter an electronic handwriting sample;
receiving the electronic handwriting sample within a signature input user interface;
synchronizing, via an encrypted communication interface and at a device, information relating to a patient that is stored in a physician-accessible database with information relating to the patient that is stored in a pharmacy database implemented by multiple servers accessible over secure networks and equipped with one or more communications devices for communication with one or more prescribing devices having point of prescription applications, and including processor control instructions for communications between the prescribing devices for prescription related data exchange;
receiving, in relation to at least one of a first medication or a second medication and via the device, a prescription input;
receiving, via the user interface, an input that authorizes electronic prescribing of a medication associated with the prescription input;
receiving, from a sponsor and in relation to the first medication, one or more publication data items that are associated with the second medication in relation to a prescribing pattern of a plurality of prescribers;

receiving, from the sponsor, one or more conditions for providing the one or more publication data items in relation to the prescribing pattern of the plurality of prescribers;

receiving, from one of the plurality of prescribers at the device, via a user interface and in relation to a first patient, a selection of the second medication;

determining, based on one or more associations between the second medication and the first medication, that the first medication is an alternative to the second medication;

identifying, by a messaging controller and based on the prescribing pattern of the plurality of prescribers in relation to the at least one of a first medication or the second medication and the selection of the second medication by the one of the plurality of prescribers in relation to the first patient in relation to the diagnosis and in relation to the prescribing pattern of the plurality of prescribers, at least one of the one or more publication data items that identifies one or more problems associated with a use of the second medication in relation to the diagnosis;

generating, based on an identification of the at least one of the one or more publication data items, an alert, the alert comprising (a) a link to the at least one of the one or more publication data items that identifies, in relation to the diagnosis, one or more problems associated with a use of the second medication, and (b) an option to select the first medication in lieu of the second medication in relation to the prescribing pattern of the plurality of prescribers, wherein the at least one of the one or more publication data items is organized in relation to the diagnosis;

providing the alert to the one of the plurality of prescribers in relation to a second patient associated with the diagnosis in view of the prescribing patterns of the plurality of prescribers in relation to at least one of a first medication or the second medication and a determination that the one or more conditions received from the sponsor are met;

generating an electronic prescription pertaining the second medication; and initiating an automatic transfer of the generated electronic prescription to a pharmacy system via a secure communication interface.

29. The non-transitory computer-readable medium of claim 28, wherein the operations further to comprise providing one or more publication data items based on a diagnosis.

30. The non-transitory computer-readable medium of claim 28, wherein the operations further comprise providing publication data items based on a treatment.

31. The non-transitory computer-readable medium of claim 28, wherein the operations further comprise providing publication data items in response to a selection of a patient for prescription.

32. The non-transitory computer-readable medium of claim 28, wherein the operations further comprise providing publication data items in response to a selection of a medication for prescription.

33. The non-transitory computer-readable medium of claim 28, wherein providing the alert to the one of the plurality of prescribers in relation to a second patient associated with the diagnosis comprises providing the alert to the one of the plurality of prescribers in relation to a second patient associated with the diagnosis prior to receiving a selection of a medication in relation to the second patient.

* * * * *